US010654927B2

(12) United States Patent
Pulé et al.

(10) Patent No.: US 10,654,927 B2
(45) Date of Patent: May 19, 2020

(54) SIGNALLING SYSTEM

(71) Applicant: UCL BUSINESS PLC, London (GB)

(72) Inventors: Martin Pulé, London (GB); Shaun Cordoba, London (GB); Khai Kong, London (GB)

(73) Assignee: UCL BUSINESS LTD, London (GB)

( * ) Notice: Subject to any disclaimer, the term of this patent is extended or adjusted under 35 U.S.C. 154(b) by 0 days.

(21) Appl. No.: 15/506,383

(22) PCT Filed: Aug. 28, 2015

(86) PCT No.: PCT/GB2015/052494
§ 371 (c)(1),
(2) Date: Feb. 24, 2017

(87) PCT Pub. No.: WO2016/030691
PCT Pub. Date: Mar. 3, 2016

(65) Prior Publication Data
US 2017/0260269 A1    Sep. 14, 2017

(30) Foreign Application Priority Data

Aug. 29, 2014 (GB) .................................. 1415347.2

(51) Int. Cl.

| | |
|---|---|
| *A61K 35/17* | (2015.01) |
| *C12N 5/10* | (2006.01) |
| *C12N 15/13* | (2006.01) |
| *C12N 15/52* | (2006.01) |
| *C12N 15/62* | (2006.01) |
| *A61K 39/00* | (2006.01) |
| *C07K 14/725* | (2006.01) |
| *C07K 14/705* | (2006.01) |
| *C07K 16/28* | (2006.01) |
| *C12N 5/0783* | (2010.01) |
| *A61K 31/65* | (2006.01) |
| *C07K 14/73* | (2006.01) |

(52) U.S. Cl.
CPC .......... *C07K 16/2803* (2013.01); *A61K 31/65* (2013.01); *A61K 35/17* (2013.01); *C07K 14/7051* (2013.01); *C07K 14/70514* (2013.01); *C12N 5/0636* (2013.01); *C07K 2317/622* (2013.01); *C07K 2319/80* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 9,856,497 B2 * | 1/2018 | Qi | C12Y 301/00 |
| 10,098,926 B2 * | 10/2018 | Pule | A61K 35/17 |
| 10,172,885 B2 * | 1/2019 | Pule | A61K 39/0011 |
| 10,172,886 B2 * | 1/2019 | Pule | A61K 39/0011 |
| 2014/0005076 A1 | 1/2014 | Gurney et al. | |
| 2016/0311907 A1 | 10/2016 | Brogdon et al. | |
| 2017/0014508 A1 | 1/2017 | Pule et al. | |
| 2017/0081411 A1 | 3/2017 | Engels et al. | |
| 2018/0016335 A1 | 1/2018 | Pule et al. | |
| 2018/0042963 A1 * | 2/2018 | Wu | C07K 16/2803 |
| 2018/0050065 A1 | 2/2018 | Pule et al. | |

FOREIGN PATENT DOCUMENTS

| | | |
|---|---|---|
| WO | WO-2014/127261 A1 | 8/2014 |
| WO | WO-2014/184143 A1 | 11/2014 |
| WO | WO-2015/142661 A1 | 9/2015 |
| WO | WO-2015/150771 A1 | 10/2015 |
| WO | WO-2016/124930 A1 | 8/2016 |
| WO | WO-2017/137758 A1 | 8/2017 |
| WO | WO-2017/137759 A1 | 8/2017 |
| WO | WO-2017/216562 A1 | 12/2017 |

OTHER PUBLICATIONS

Janus et al Cell Mol Biol Lett. 2005;10(3):479-98. The mammalian target of the rapamycin (mTOR) kinase pathway: its role in tumourigenesis and targeted antitumour therapy.*
Wilkie et al J Clin Immunol (2012) 32:1059-1070 Dual Targeting of ErbB2 and MUC1 in Breast Cancer Using Chimeric Antigen Receptors Engineered to Provide Complementary Signaling.*
Dotti et al Immunol Rev. Jan. 2014 ; 257(1) pp. 1-30; Design and Development of Therapies using Chimeric Antigen Receptor-Expressing T cells.*
Goeke et al., Short peptides act as inducers, anti-inducers and corepressors of tet repressor Journal of Molecular Biology vol. 416, Issue 1, Feb. 10, 2012, pp. 33-45.*
Chicaybam et al., A conditional system for the activation of lymphocytes expressing activating and inhibitory CARs. *Hum. Gene Ther.* 21(10): 1418 (2010).
Cordoba et al., Chimeric antigen receptor logical and gate based on CD45/CD148 phosphatases. *Molec. Ther.* 22(suppl. 1): S59 (2014).
International Preliminary Report on Patentability, International Application No. PCT/GB2015/052494, dated Feb. 28, 2017.

(Continued)

*Primary Examiner* — Maria G Leavitt
(74) *Attorney, Agent, or Firm* — Marshall, Gerstein & Borun LLP

(57) ABSTRACT

The present invention provides a chimeric antigen receptor (CAR) signalling system comprising; (i) a receptor component comprising an antigen binding domain, a transmembrane domain and a first binding domain; and (ii) an intracellular signalling component comprising a signalling domain and a second binding domain which specifically binds the first binding domain of the receptor component; wherein, binding of the first and second binding domains is disrupted by the presence of an agent, such that in the absence of the agent the receptor component and the signalling component heterodimerize and binding of the antigen binding domain to antigen results in signalling through the signalling domain, whereas in the presence of the agent the receptor component and the signalling component do not heterodimerize and binding of the antigen binding domain to antigen does not result in signalling through the signalling domain.

16 Claims, 15 Drawing Sheets

Specification includes a Sequence Listing.

(56) References Cited

OTHER PUBLICATIONS

International Search Report and Written Opinion, International Application No. PCT/GB2015/052494, dated Oct. 14, 2015.
Klotzsche et al., A peptide triggers allostery in tet repressor by binding to a unique site, J. Biol. Chem., 280(26):24591-9 (2005).
Luckner et al., How an agonist peptide mimics the antibiotic tetracycline to induce Tet-repressor. *J. Molec. Biol.* 368(3): 780-90 (2007).
Rivera et al., A humanized system for pharmacologic control of gene expression, Nat. Med., 2(9):1028-32 (1996).
White et al., Protein-protein interactions as targets for small-molecule therapeutics in cancer, Expert Rev. Mol. Med., 10:e8 (2008).
Amrolia et al, "Chimeric antigen receptor T cells for ALL," Lancet 385(9967):488-490 (2015).
Budde et al., "Combining a CD20 chimeric antigen receptor and an inducible caspase 9 suicide switch to improve the efficacy and safety of T cell adoptive immunotherpay for lymphoma," PLOS One 8(12):e82742, 10 pages (2013).
Casucci et al., "Suicide Gene Therapy to increase the safety of chimeric antigen receptor-redirected T Lymphocytes," Journal of Cancer 2:378-382 (2011).
Chicaybam et al., "Constructions and validation of an activating and inhibitory chimeric antigen receptor (CAR) system," Cancer Research 74(Suppl 19) Abstract #2797 (2014).
Davila et al, "Efficacy and toxicity management of 19-28z CAR T cell therapy in B cell acute lymphoblastic leukemia," Sci. Transl. Med., 6(224):224ra25, 23 pages (2014).
Federov et al., "Inhibitory Chimeric Antigen Receptors (iCARs) Limit Undersirable Side Effects of T-Cell Therapies," Experimental Hematology, 42nd Annual Scientific Meeting of the ISEH—Society for Hematology and Stem Cells, 41(2):Abstract S75 (2013).
Fedorov et al., "PD-1- and CTLA-4-Based Inhibitory Chimeric Antigen Receptors (iCARs) Divert Off-Target Immunotherapy Responses," Sci Transl Med. 5(215):215ra172 (2013).
Jena et al, "Redirecting T-cell specificity by introducing a tumor-specific chimeric antgen receptor," Blood 116(7):1035-1044 (2010).
Kershaw et al., "Clinical application of genetically modified T cells in cancer therapy," Clinical Translation Immunology 3:e16, 8 pages (2014).
Klotzsche et al., "Efficient and exclusive induction of Tet repressor by the oligopeptide Tip results from co-variation of their interaction site," Nucleic Acids Research 35(12):3945-3952 (2007).
Kochenderfer et al, "Chemotherapy-refractory diffuse large B-cell lymphoma and indolent B-cell malignancies can be effectively treated with autologous T cells expressing an anti-CD19 chimeric antigen receptor," J. Clin. Oncol. 33(6):540-549 (2015).
Maude et al, "Chimeric antigen receptor T cells for sustained remissions in leukemia," 371(16):1507-1517 (2014).
Ramos et al., "Chimeric antigen receptor (CAR)-engineered lymphocytes for cancer therapy," Expert Opin. Biol. Ther. 11(7):855-873 (2011).
Chang et al., A general method for facilitating heterodimeric pairing between two proteins: application to expression of alpha and beta T-cell receptor extracellular segments, *Proc. Natl. Acad. Sci. USA.* 91:11408-12 (1994).
Clackson et al., Redesigning an FKBP-ligand interface to generate chemical dimerizers with novel specificity, *Proc. Natl. Acad. Sci. USA.* 95:10437-42 (1998).
Deyev et al., Design of multivalent complexes using the barnase-barstar module, *Nat. Biotechnol.* 21:1486-92 (2003).
Gendreizig et al., Induced protein dimerization in vivo through covalent labeling, *J. Am. Chem. Soc.* 125:14970-1 (2003).
Jensen et al., Design and implementation of adoptive therapy with chimeric antigen receptor-modified T cells, *Immunol. Rev.* 257:127-44 (2014).
Lanitis et al., Chimeric antigen receptor T Cells with dissociated signaling domains exhibit focused antitumor activity with reduced potential for toxicity in vivo, *Cancer Immunol. Res.* 1:43-53 (2013).
Rossi et al., Stably tethered multifunctional structures of defined composition made by the dock and lock method for use in cancer targeting, *Proc. Natl. Acad. Sci. USA.* 103:6841-6 (2006).
Rossi et al., The dock-and-lock method combines recombinant engineering with site-specific covalent conjugation to generate multifunctional structures, *Bioconjug. Chem.* 23:309-23 (2012).
Bager et al., "Protein Conformational Change Delayed by Steric Hindrance from an N-Linked Glycan," Journal of Molecular Biology 425, pp. 2867-2877 (2013).
Russian Office Action dated Nov. 12, 2019, issued in Russian Application No. 2017105515/10(009907).
U.S. Appl. No. 15/301,148 (US-2017-0014508 A1), filed Sep. 30, 2016.
U.S. Appl. No. 15/548,340 (US-2018-0016335 A1), filed Aug. 2, 2017.

\* cited by examiner (a) WTWNAYAFAAPS-GGGS-[Protein]

SIGNALLING SYSTEM

FIELD OF THE INVENTION

The present invention relates to a chimeric antigen receptor signalling system.

BACKGROUND TO THE INVENTION

Traditionally, antigen-specific T-cells have been generated by selective expansion of peripheral blood T-cells natively specific for the target antigen. However, it is difficult and quite often impossible to select and expand large numbers of T-cells specific for most cancer antigens. Gene-therapy with integrating vectors affords a solution to this problem as transgenic expression of Chimeric Antigen Receptor (CAR) allows generation of large numbers of T cells specific to any surface antigen by ex vivo viral vector transduction of a bulk population of peripheral blood T-cells.

Chimeric antigen receptors are proteins which graft the specificity of a monoclonal antibody (mAb) to the effector function of a T-cell. Their usual form is that of a type I transmembrane domain protein with an antigen recognizing amino terminus, a spacer, a transmembrane domain all connected to a compound endodomain which transmits T-cell survival and activation signals (see FIG. 1A).

The most common forms of these molecules are fusions of single-chain variable fragments (scFv) derived from monoclonal antibodies which recognize a target antigen, fused via a spacer and a trans-membrane domain to a signalling endodomain. Such molecules result in activation of the T-cell in response to recognition by the scFv of its target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers.

A number of toxicities have been reported from CAR studies, and additional theoretical toxicities exist. Such toxicities include immunological toxicity caused by sustained intense activation of the CAR T-cells resulting in a macrophage activation syndrome (MAS) and "On-target off-tumour" toxicity i.e. recognition of the target antigen on normal tissues.

MAS is presumed to be caused by persistent antigen-driven activation and proliferation of T-cells which in turn release copious inflammatory cytokines leading to hyper-activation of macrophages and a feed-forward cycle of immune activation. A large spike in serum IL-6 is characteristic and the syndrome can result in a severe systemic illness requiring ICU admission.

On-target off-tumour toxicity has been reported with other CARs, for example a group of patients treated with a CAR against the renal cell carcinoma antigen CAIX developed unexpected and treatment limiting biliary toxicity. Two fatalities have been reported with CAR studies: one patient died of a respiratory distress syndrome which occurred immediately post-infusion of a large dose of 3rd generation anti-ERBB2 CAR T-cells; a further patient died in a different study after a possible cytokine storm following treatment of CLL with a second generation anti-CD19 CAR.

These toxicities are very difficult to predict even with detailed animal studies or non-human primate work. Crucially, unlike small molecules and biologics, CAR T-cells do not have a half-life and one cannot cease administration and wait for the agent to breakdown/become excreted. CAR T-cells are autonomous and can engraft and proliferate. Toxicity can therefore be progressive and fulminant.

Suicide genes are genetically expressed elements which can conditionally destroy cells which express them. Examples include Herpes-simplex virus thymidine kinase, which renders cells susceptible to Ganciclovir; inducible Caspase 9, which renders cells susceptible to a small molecular homodimerizer and CD20 and RQR8, which renders cells susceptible to Rituximab.

This technology adds a certain amount of safety to CAR T-cell therapy, however there are limitations. Firstly, it is a binary approach wherein all the CAR T-cells are destroyed upon addition of the suicide agent. In addition, medicinal therapeutics often have a therapeutic window. With a suicide gene the potency of the product cannot be tuned such that efficacy with tolerable toxicity can be achieved. Secondly, it is not clear whether a suicide gene would help with some of the immune-toxicities described above: for instance by the time a macrophage activation syndrome had been triggered, it may well no longer need the CAR T-cells to perpetuate and the suicide gene would no longer be helpful. The more acute cytokine release syndromes probably occur too quickly for the suicide gene to work.

There is thus a need for alternative methods for controlling CAR T-cells that are not associated with the disadvantages and problems mentioned above.

DESCRIPTION OF THE FIGURES

FIG. 2—Structures of TetR and TiP. (a) sequence of TiP attached at the amino-terminus of an arbitrary protein; (b) Crystallography derived structure of TiP interacting with TetR (from PDB 2NS8 and Luckner et al (J. Mol. Biol. 368, 780-790 (2007)). TiP can be seen engaged deep within the TetR homodimer associating with many of the residues tetracycline associates with.

SUMMARY OF ASPECTS OF THE INVENTION

Figure 1:
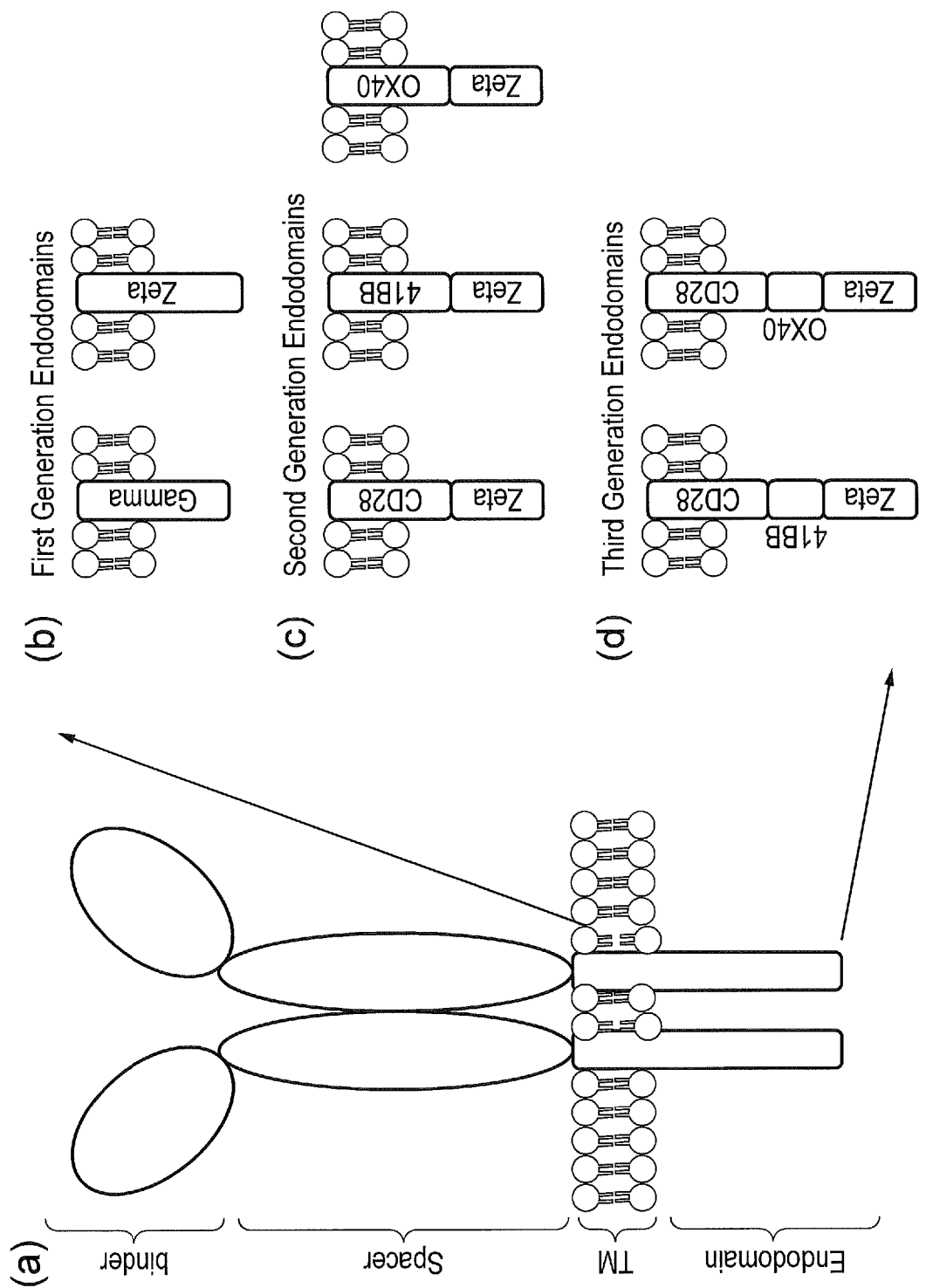
FIG. 1—a) Schematic diagram illustrating a classical CAR. (b) to (d): Different generations and permutations of CAR endodomains: (b) initial designs transmitted ITAM signals alone through FɛER1-γ or CD3ζ endodomain, while later designs transmitted additional (c) one or (d) two co-stimulatory signals in the same compound endodomain.
Figure 2:
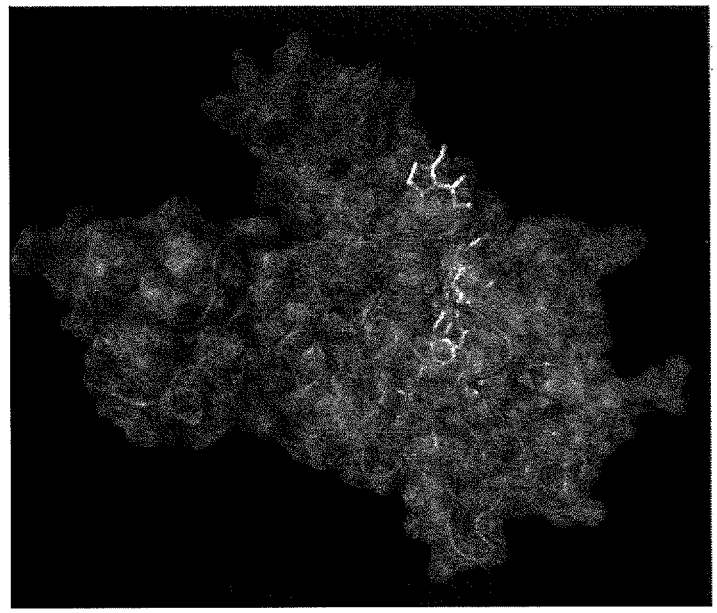

The present inventors have found that it is possible to separate the antigen-recognition and signalling components of a CAR to produce a system in which signalling can be rapidly inhibited/terminated despite continued binding of antigen to an antigen-recognition component of the CAR system. This inhibition of signalling occurs in the presence of an agent, such as a small molecule, which inhibits the co-localisation and interaction which would otherwise occur between an extracellular antigen-binding component (referred to herein as the receptor component) and an intracellular signalling component of the CAR.

Thus in a first aspect the present invention provides a chimeric antigen receptor (CAR) system comprising;
  (i) a receptor component comprising an antigen binding domain, a transmembrane domain and a first binding domain; and
  (ii) an intracellular signalling component comprising a signalling domain and a second binding domain which specifically binds the first binding domain of the receptor component;
wherein, binding of the first and second binding domains is disrupted by the presence of an agent, such that in the absence of the agent the receptor component and the signalling component heterodimerize and binding of the antigen binding domain to antigen results in signalling through the signalling domain, whereas in the presence of the agent the receptor component and the signalling component do not heterodimerize and binding of the antigen binding domain to antigen does not result in signalling through the signalling domain.

The receptor component may comprise a linker between the transmembrane domain and the first binding domain.

The linker may comprise or consist of the sequence shown as SEQ ID NO: 3.

The first binding domain may comprise Tet Repressor Protein (TetR) or a variant thereof and the second binding domain may comprise TetR inducing Peptide (TiP, as described by Klotzsche et al; The Journal of biological chemistry; 2005; 280(26); 24591-9) (TiP); or vice versa. In this case the agent may be tetracycline, doxycycline or minocycline or an analogue thereof.

The receptor component may comprise two first binding domains which are TetR domains. The two TetR domains may be separated by a linker. Each TetR domain may have a different affinity for the agent.

The CAR system of the first aspect of the invention may comprise multiple receptor components, each recognizing a different antigen.

The first binding domains of the multiple receptor components may differ in binding to the second binding domain of the signalling component such that each antigen propagates different signalling strengths.

The first binding domains of the multiple receptor components may differ in binding to the agent such that each antigen propagates different signalling strengths in the presence of the agent.

The signalling domain of the signalling component may comprise a single endodomain selected from CD3 zeta endodomain, CD28 endodomain, 41BB endodomain and OX40 endodomain.

The signalling domain of the signalling component may comprise at least one of CD3 zeta endodomain, CD28 endodomain, 41BB endodomain and OX40 endodomain.

The CAR system of the first aspect of the invention may comprise a plurality of signalling components, each comprising a signalling domain and a second binding domain, wherein the second binding domains each recognise the same first binding domain of the receptor component but the signalling domains comprise different endodomains.

The plurality of signalling components may comprise a plurality of second binding domains, each of which independently recognises the first binding domain of the receptor component with different affinities.

In a second aspect the present invention provides a receptor component suitable for use in the CAR system of the first aspect of the invention which comprises an antigen-binding domain, a transmembrane domain and a first binding domain.

In a third aspect the present invention provides a signalling component suitable for use in the CAR system of the first aspect of the invention which comprises a signalling domain and a second binding domain.

In a fourth aspect the present invention provides a nucleic acid sequence encoding the receptor component according to the second aspect of the invention.

In a fifth aspect the present invention provides a nucleic acid sequence encoding the signalling component according to the third aspect of the invention.

In a sixth aspect the present invention provides a nucleic acid sequence encoding a CAR system of the first aspect of the invention, wherein the receptor component and signalling component are co-expressed by means of a self-cleaving peptide which is cleaved between the receptor component and the signalling component after translation.

In a seventh aspect the present invention provides a vector comprising a nucleic acid sequence according to the fourth to sixth aspects of the invention.

In an eighth aspect the present invention provides a retroviral vector or a lentiviral vector or a transposon comprising a vector according to the seventh aspect of the invention.

In a ninth aspect the present invention provides a T cell or NK cell which expresses a receptor component according to the second aspect of the invention and a signalling component according to the third aspect of the invention.

The T cell or NK cell may comprise a nucleic acid according to the fourth to sixth aspects of the invention or a vector according to the seventh or eighth aspect of the invention.

In a tenth aspect the present invention provides a pharmaceutical composition comprising a plurality of T cells or NK cells according to the ninth aspect of the invention.

In an eleventh aspect the present invention provides a pharmaceutical composition according to the tenth aspect of the invention for use in treating and/or preventing a disease.

In a twelfth aspect the present invention relates to a method for treating and/or preventing a disease, which comprises the step of administering a pharmaceutical composition according to the tenth aspect of the invention to a subject.

The method according to the twelfth aspect of the invention may comprise the following steps:

(i) isolation of a T cell or NK containing sample;
(ii) transduction or transfection of the T or NK cells with a nucleic acid sequence according to any of the fourth to sixth aspects of the invention or a vector according to the seventh or eighth aspect of the invention; and
(iii) administering the T cells or NK cells from (ii) to a subject.

The method may involve administration of T cells/NK cells to a subject, which Tcells/NK cells have been previously isolated from the subject and transduced/transfected with a nucleic acid sequence according to any of the fourth to sixth aspects of the invention or a vector according to the seventh or eighth aspect of the invention.

The method according to the twelfth aspect of the invention may involve monitoring toxic activity in the subject and comprise the step of administering an agent for use in the CAR system of the first aspect of the invention to the subject to reduce adverse toxic effects.

The method may involve monitoring the progression of disease and/or monitoring toxic activity in the subject and comprise the step of administering an agent for use in the CAR system of the first aspect of the invention to the subject to provide acceptable levels of disease progression and/or toxic activity.

In the use of a pharmaceutical composition according to the tenth aspect of the invention or a method according to the twelfth aspect of the invention, the disease may be cancer.

In a thirteenth aspect the present invention relates to the use of a pharmaceutical composition according to the tenth aspect of the invention in the manufacture of a medicament for the treatment and/or prevention of a disease.

In a fourteenth aspect the present invention provides a kit which comprises a nucleic acid according to the fourth to sixth aspects of the invention or a vector according to the seventh of eighth aspect of the invention.

In a fifteenth aspect the present invention relates to a method for making a T or NK cell according to the ninth aspect of the invention, which comprises the step of introducing a nucleic acid sequence according to fourth to sixth aspect of the invention or the vector according to the seventh or eighth aspect of the invention into a T or NK cell.

The T or NK cell may be from a sample isolated from a subject.

In a sixteenth aspect the present invention relates to a method for inhibiting the CAR system according to the first aspect of the invention in a subject which comprises a T or NK cell according to the ninth aspect of the invention which method comprises the step of administering the agent to the subject.

The present invention therefore provides a CAR system in which signalling can be inhibited in the presence of an agent, for example a small molecule, which prevents co-localisation of the receptor component and signalling component. This allows CAR signalling and thus the potency of CAR cells to be reversibly terminated in a controllable manner in order to avoid potential toxic effects associated with unabated CAR signalling. Further the present system also allows the potency of CAR cells to be controlled pharmacologically and tuned to an acceptable balance between achieving the desired therapeutic effect and avoiding unwanted toxicities.

DETAILED DESCRIPTION

Chimeric Antigen Receptors (CARs)

Classical CARs, which are shown schematically in FIG. 1, are chimeric type I trans-membrane proteins which connect an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like antigen binding site. A spacer domain may be necessary to isolate the binder from the membrane and to allow it a suitable orientation. A common spacer domain used is the Fc of IgG1. More compact spacers can suffice e.g. the stalk from CD8a and even just the IgG1 hinge alone, depending on the antigen. A trans-membrane domain anchors the protein in the cell membrane and connects the spacer to the endodomain.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41BB which transmit survival signals. Even more potent third generation CARs have now been described which have endodomains capable of transmitting activation, proliferation and survival signals.

CAR-encoding nucleic acids may be transferred to T cells using, for example, retroviral vectors. In this way, a large number of antigen-specific T cells can be generated for adoptive cell transfer. When the CAR binds the target-antigen, this results in the transmission of an activating signal to the T-cell it is expressed on. Thus the CAR directs the specificity and cytotoxicity of the T cell towards cells expressing the targeted antigen.

In a first aspect, the present invention relates to a CAR system in which the antigen-recognizing/antigen binding domain and transmembrane domain are provided on a first molecule (termed herein 'receptor component'), which localizes to the cell membrane. The intracellular signalling domain is provided on a second, intracellular molecule (termed herein 'signalling component').

Importantly, the receptor component comprises a first binding domain and the signalling component comprises a second binding domain which specifically binds to the first binding domain of the receptor component. Thus binding of the first binding domain to the second binding domain causes heterodimerization and co-localization of the receptor component and the signalling component. When antigen binds to the antigen binding domain of the receptor component there is signalling through the signalling component.

The first or second binding domain is also capable of binding a further agent in addition to the reciprocal binding domain. The further agent may be, for example, a small molecule. The binding between the agent and the first or second binding domain is of a higher affinity than the binding between the first binding domain and the second binding domain. Thus, when the agent is present it preferentially binds to the first or second binding domain and inhibits/disrupts the heterodimerization between the receptor component and the signalling component. When antigen binds to the antigen binding domain of the receptor component in the presence of the further agent there is no signalling through the signalling component.

Specifically, in the presence of the agent, the receptor component and signalling component are located in a stochastically dispersed manner and binding of antigen by the antigen-binding domain of the receptor component does not result in signalling through the signaling component.

Herein 'co-localization' or 'heterodimerization' of the receptor and signalling components is analogous to ligation/recruitment of the signalling component to the receptor component via binding of the first binding domain of the receptor component and the second binding domain of the signalling component.

Antigen binding by the receptor component in the presence of the agent may be termed as resulting in 'non-productive' signalling through the signalling component. Such signalling does not result in cell activation, for example T cell activation. Antigen binding by the receptor component in the absence of the agent may be termed as resulting in 'productive' signalling through the signalling component. This signalling results in T-cell activation, triggering for example target cell killing and T cell activation.

Antigen binding by the receptor component in the absence of the agent may result in signalling through the signalling component which is 2, 5, 10, 50, 100, 1,000 or 10,000-fold higher than the signalling which occurs when antigen is bound by the receptor component in the presence of the agent.

Signalling through the signalling component may be determined by a variety of methods known in the art. Such methods include assaying signal transduction, for example assaying levels of specific protein tyrosine kinases (PTKs), breakdown of phosphatidylinositol 4,5-biphosphate ($PIP_2$), activation of protein kinase C (PKC) and elevation of intracellular calcium ion concentration. Functional readouts, such as clonal expansion of T cells, upregulation of activation markers on the cell surface, differentiation into effector cells and induction of cytotoxicity or cytokine secretion may also be utilised. As an illustration, in the present examples the inventors determined levels of interleukin-2 (IL-2) produced by T-cells expressing a receptor component and signalling component of the CAR system according to the present invention upon binding of antigen to the receptor component in the presence of varying concentrations of an agent.

First Binding Domain, Second Binding Domain and Agent

The first binding domain, second binding domain and agent of the present CAR system may be any combination of molecules/peptides/domains which enable the selective co-localization and dimerization of the receptor component and signalling component in the absence of the agent.

As such, the first binding domain and second binding domain are capable of specifically binding.

The signalling system of the present invention is not limited by the arrangement of a specific dimerization system. The receptor component may comprise either the first binding domain or the second binding domain of a given dimerization system so long as the signalling component comprises the corresponding, complementary binding domain which enables the receptor component and signalling component to co-localize in the absence of the agent.

The first binding domain and second binding domain may be a peptide domain and a peptide binding domain; or vice versa. The peptide domain and peptide binding domain may be any combination of peptides/domains which are capable of specific binding.

The agent is a molecule, for example a small molecule, which is capable of specifically binding to the first binding domain or the second binding domain at a higher affinity than the binding between the first binding domain and the second binding domain.

For example, the binding system may be based on a peptide:peptide binding domain system. The first or second binding domain may comprise the peptide binding domain and the other binding domain may comprise a peptide mimic which binds the peptide binding domain with lower affinity than the peptide. The use of peptide as agent disrupts the binding of the peptide mimic to the peptide binding domain through competitive binding. The peptide mimic may have a similar amino acid sequence to the "wild-type" peptide, but with one of more amino acid changes to reduce binding affinity for the peptide binding domain.

For example, the agent may bind the first binding domain or the second binding domain with at least 10, 20, 50, 100, 1000 or 10000-fold greater affinity than the affinity between the first binding domain and the second binding domain.

The agent may be any pharmaceutically acceptable molecule which preferentially binds the first binding domain or the second binding domain with a higher affinity than the affinity between the first binding domain and the second binding domain.

The agent is capable of being delivered to the cytoplasm of a target cell and being available for intracellular binding.

The agent may be capable of crossing the blood-brain barrier.

Small molecule systems for controlling the co-localization of peptides are known in the art, for example the Tet repressor (TetR), TetR interacting protein (TiP), tetracycline system (Klotzsche et al.; J. Biol. Chem. 280, 24591-24599 (2005); Luckner et al.; J. Mol. Biol. 368, 780-790 (2007)).

The Tet Repressor (TetR) System

The Tet operon is a well-known biological operon which has been adapted for use in mammalian cells. The TetR binds tetracycline as a homodimer and undergoes a conformational change which then modulates the DNA binding of the TetR molecules. Klotzsche et al. (as above), described a phage-display derived peptide which activates the TetR. This protein (TetR interacting protein/TiP) has a binding site in TetR which overlaps, but is not identical to, the tetracycline binding site (Luckner et al.; as above). Thus TiP and tetracycline compete for binding of TetR.

In the present CAR system the first binding domain of the receptor component may be TetR or TiP, providing that the second binding domain of the signalling component is the corresponding, complementary binding partner. For example if the first binding domain of the receptor component is TetR, the second binding domain of the signalling component is TiP. If the first binding domain of the receptor component is TiP, the second binding domain of the signalling component is TetR.

For example, the first binding domain or second binding domain may comprise the sequence shown as SEQ ID NO: 1 or SEQ ID NO: 2:

TetR
SEQ ID NO: 1
MSRLDKSKVINSALELLNEVGIEGLTTRKLAQKLGVEQPTLYWHVKNKRA

LLDALAIEMLDRHHTHFCPLEGESWQDFLRNNAKSFRCALLSHRDGAKVH

LGTRPTEKQYETLENQLAFLCQQGFSLENALYALSAVGH

TiP
SEQ ID NO: 2
MWTWNAYAFAAPSGGGS

TetR must homodimerize in order to function. Thus when the first binding domain on the receptor component is TetR, the receptor component may comprise a linker between the transmembrane domain and the first binding domain (TetR). The linker enables TetR to homodimerize with a TetR from a neighbouring receptor component and orient in the correct direction.

The linker may be the sequence shown as SEQ ID NO: 3.

modified CD4 endodomain
SEQ ID NO: 3
ALIVLGGVAGLLLFIGLGIFFCVRCRHRRRQAERMAQIKRVVSEKKTAQAP

HRFQKTCSPI

The linker may alternatively comprise an alternative linker sequence which has similar length and/or domain spacing properties as the sequence shown as SEQ ID NO: 3.

The linker may have at least 80%, 85%, 90%, 95%, 98% or 99% sequence identity to SEQ ID NO: 3 providing it provides the function of enabling TetR to homodimerize with a TetR from a neighbouring receptor component and orient in the correct direction.

One potential disadvantage of the TetR/TiP system is TetR is xenogenic and immunogenic. The TetR sequence may therefore be a variant which is less immunogenic but retains the ability to specifically bind TiP.

Where the first and second binding domains are TetR or TiP or a variant thereof, the agent may be tetracycline, doxycycline, minocycline or an analogue thereof.

An analogue refers to a variant of tetracycline, doxycycline or minocycline which retains the ability to specifically bind to TetR.

Other combinations of binding domains and agents which may be used in the present CAR system are known in the art. For example, the CAR system may use a streptavidin/biotin-based binding system.

Streptavidin-Binding Epitope

The first or second binding domain may comprise one or more streptavidin-binding epitope(s). The other binding domain may comprise a biotin mimic.

Streptavidin is a 52.8 kDa protein from the bacterium *Streptomyces avidinii*. Streptavidin homo-tetramers have a very high affinity for biotin (vitamin B7 or vitamin H), with a dissociation constant (Kd)~$10^{-15}$ M. The biotin mimic has a lower affinity for streptavidin than wild-type biotin, so that biotin itself can be used as the agent to disrupt or prevent heterodimerisation between the streptavidin domain and the biotin mimic domain. The biotin mimic may bind streptavidin with for example with a Kd of 1 nM to 100 uM.

The 'biotin mimic' domain may, for example, comprise a short peptide sequence (for example 6 to 20, 6 to 18, 8 to 18 or 8 to 15 amino acids) which specifically binds to streptavidin.

The biotin mimic may comprise a sequence as shown in Table 1.

TABLE 1

Biotin mimicking peptides.

| name | Sequence | affinity |
| --- | --- | --- |
| Long nanotag | DVEAWLDERVPLVET (SEQ ID NO: 4) | 3.6 nM |
| Short nanotag | DVEAWLGAR (SEQ ID NO: 5) | 17 nM |
| Streptag | WRHPQFGG (SEQ ID NO: 6) | |
| streptag II | WSHPQFEK (SEQ ID NO: 7) | 72 uM |
| SBP-tag | MDEKTTGWRGGHVVEGLAGELEQLRARLEHHPQGQREP (SEQ ID NO: 8) | 2.5 nM |
| ccstreptag | CHPQGPPC (SEQ ID NO: 9) | |
| flankedccstreptag | AECHPQGPPCIEGRK (SEQ ID NO: 10) | 230 nM |

The biotin mimic may be selected from the following group: StreptagII, Flankedccstreptag and ccstreptag.

The streptavidin domain may comprise streptavidin having the sequence shown as SEQ ID No. 11 or a fragment or variant thereof which retains the ability to bind biotin.

Full length Streptavidin has 159 amino acids. The N and C termini of the 159 residue full-length protein are processed to give a shorter 'core' streptavidin, usually composed of residues 13-139; removal of the N and C termini is necessary for the high biotin-binding affinity.

The sequence of "core" streptavidin (residues 13-139) is shown as SEQ ID No. 11

SEQ ID No. 11
EAGITGTWYNQLGSTFIVTAGADGALTGTYESAVGNAESRYVLTGRYDS
APATDGSGTALGVVTVAWKNNYRNAHSATTWSGQYVGGAEARINTQWLL
TSGTTEANAWKSTLVGHDTFTKVKPSAAS

Streptavidin exists in nature as a homo-tetramer. The secondary structure of a streptavidin monomer is composed of eight antiparallel β-strands, which fold to give an antiparallel beta barrel tertiary structure. A biotin binding-site is located at one end of each β-barrel. Four identical streptavidin monomers (i.e. four identical β-barrels) associate to give streptavidin's tetrameric quaternary structure. The biotin binding-site in each barrel consists of residues from the interior of the barrel, together with a conserved Trp120 from neighbouring subunit. In this way, each subunit contributes to the binding site on the neighbouring subunit, and so the tetramer can also be considered a dimer of functional dimers.

The streptavidin domain of the CAR system of the present invention may consist essentially of a streptavidin monomer, dimer or tetramer.

The sequence of the streptavidin monomer, dimer or tetramer may comprise all or part of the sequence shown as SEQ ID No. 11, or a variant thereof which retains the capacity to bind biotin.

A variant streptavidin sequence may have at least 70, 80, 90, 95 or 99% identity to SEQ ID No. 11 or a functional portion thereof. Variant streptavidin may comprise one or more of the following amino acids, which are involved in biotin binding: residues Asn23, Tyr43, Ser27, Ser45, Asn49, Ser88, Thr90 and Asp128. Variant streptavidin may, for example, comprise all 8 of these residues. Where variant streptavidin is present in the binding domain as a dimer or tetramer, it may also comprise Trp120 which is involved in biotin binding by the neighbouring subunit.

Small molecules agents which disrupt protein-protein interactions have long been developed for pharmaceutical purpose (reviewed by Vassilev et al; Small-Molecule Inhibitors of Protein-Protein Interactions ISBN: 978-3-642-17082-9). A CAR system as described may use such a small molecule. The proteins or peptides whose interaction is disrupted (or relevant fragments of these proteins) can be used as the first and/or second binding domains and the small molecule may be used as the agent which inhibits CAR activation. Such a system may be varied by altering the small molecule and proteins such the system functions as described but the small molecule is devoid of unwanted pharmacological activity (e.g. in a manner similar to that described by Rivera et al (Nature Med; 1996; 2; 1028-1032).

A list of proteins/peptides whose interaction is disruptable using an agent such as a small molecule is given in Table 2. These disruptable protein-protein interactions (PPI) may be used in the CAR system of the present invention. Further information on these PPIs is available from White et al 2008 (Expert Rev. Mol. Med. 10:e8).

TABLE 2

| Interacting Protein 1 | Interacting Protein 2 | Inhibitor of PPI |
| --- | --- | --- |
| p53 | MDM2 | Nutlin |
| Anti-apoptotic Bcl2 member | Apoptotic Bcl2 member | GX015 and ABT-737 |
| Caspase-3, -7 or -9 | X-linked inhibitor of apoptosis protein (XIAP) | DIABLO and DIABLO mimetics |
| RAS | RAF | Furano-indene derivative |
| FR2-7 | PD2 domain of DVL | FJ9 |
| T-cell factor (TCF) | Cyclic AMP response element binding protein (CBP) | ICG-001 |

Second binding domains which competitively bind to the same first binding domain as the agents described above, and thus may be used to co-localise the receptor component and signalling component of the present signalling system in the absence of the agent, may be identified using techniques and methods which are well known in the art. For example such second binding domains may be identified by display of a single domain VHH library.

The first binding domain and/or second binding domain of the present signalling system may comprise a variant(s) which is able to specifically bind to the reciprocal binding domain and thus facilitate co-localisation of the receptor component and signalling component.

Variant sequences may have at least 80%, 85%, 90%, 95%, 98% of 99% sequence identity to the wild-type sequence, provided that the sequences provide an effective dimerization system. That is, provided that the sequences facilitate sufficient co-localisation of the receptor and signalling components, in the absence of the agent, for productive signalling to occur upon binding of the antigen-binding domain to antigen.

The present invention also relates to a method for inhibiting the CAR system of the first aspect of the invention, which method comprises the step of administering the agent. As described above, administration of the agent results in a disruption of the co-localization between the receptor component and the signalling component, such that signalling through the signalling component is inhibited even upon binding of antigen to the antigen binding domain.

The first and second binding domains may facilitate signalling through the CAR system which is proportional to the concentration of the agent which is present. Thus, whilst the agent binds the first binding domain or the second binding domain with a higher affinity than binding affinity between the first and second binding domains, co-localization of the receptor and signalling components may not be completely ablated in the presence of low concentrations of the agent. For example, low concentrations of the agent may decrease the total level of signalling in response to antigen without completely inhibiting it. The specific concentrations of agent will differ depending on the level of signalling required and the specific binding domains and agent. Levels of signalling and the correlation with concentration of agent can be determined using methods known in the art, as described above.

Receptor Component

The present invention provides a receptor component comprising an antigen-binding domain, an optional spacer domain, a transmembrane domain and a first biding domain. When expressed in a cell, the receptor component localises to the cell membrane. Here, the antigen-binding domain of the molecule is orientated on the extracellular side of the membrane and the first binding domain is localised to the intracellular side of the membrane.

The receptor component therefore provides the antigen-binding function of the CAR system of the present invention.

Antigen Binding Domain

The antigen-binding domain is the portion of a classical CAR which recognizes antigen. In the signalling system of the present invention the antigen-binding is located within the receptor component.

Numerous antigen-binding domains are known in the art, including those based on the antigen binding site of an antibody, antibody mimetics, and T-cell receptors. For example, the antigen-binding domain may comprise: a single-chain variable fragment (scFv) derived from a monoclonal antibody; a natural ligand of the target antigen; a peptide with sufficient affinity for the target; a single domain binder such as a camelid; an artificial binder single as a Darpin; or a single-chain derived from a T-cell receptor.

Various tumour associated antigens (TAA) are known, as shown in the following Table 1. The antigen-binding domain used in the present invention may be a domain which is capable of binding a TAA as indicated therein.

TABLE 1

| Cancer type | TAA |
| --- | --- |
| Diffuse Large B-cell Lymphoma | CD19, CD20 |
| Breast cancer | ErbB2, MUC1 |
| AML | CD13, CD33 |
| Neuroblastoma | GD2, NCAM, ALK, GD2 |
| B-CLL | CD19, CD52, CD160 |
| Colorectal cancer | Folate binding protein, CA-125 |
| Chronic Lymphocytic Leukaemia | CD5, CD19 |
| Glioma | EGFR, Vimentin |
| Multiple myeloma | BCMA, CD138 |
| Renal Cell Carcinoma | Carbonic anhydrase IX, G250 |
| Prostate cancer | PSMA |
| Bowel cancer | A33 |

Transmembrane Domain

The transmembrane domain is the sequence of a classical CAR that spans the membrane. In the signalling system of the present invention the transmembrane domain is located in the receptor component. It may comprise a hydrophobic alpha helix. The transmembrane domain may be derived from CD28, which gives good receptor stability.

Signal Peptide

The receptor component of the CAR system of the present invention may comprise a signal peptide so that when the receptor component is expressed in a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

The signal peptide may comprise the sequence shown as SEQ ID NO: 12, 13 or 14 or a variant thereof having 5, 4, 3, 2 or 1 amino acid mutations (insertions, substitutions or additions) provided that the signal peptide still functions to cause cell surface expression of the CAR.

```
SEQ ID NO: 12:
MGTSLLCWMALCLLGADHADG
```

The signal peptide of SEQ ID NO: 12 is compact and highly efficient. It is predicted to give about 95% cleavage after the terminal glycine, giving efficient removal by signal peptidase.

```
SEQ ID NO: 13:
MSLPVTALLLPLALLLHAARP
```

The signal peptide of SEQ ID NO: 13 is derived from IgG1.

```
SEQ ID NO: 14:
MAVPTQVLGLLLLWLTDARC
```

The signal peptide of SEQ ID NO: 14 is derived from CD8.

Spacer Domain

The CAR system described herein may comprise a spacer sequence to connect the antigen-binding domain with the transmembrane domain in the receptor component. A flexible spacer allows the antigen-binding domain to orient in different directions to facilitate binding.

The spacer sequence may, for example, comprise an IgG1 Fc region, an IgG1 hinge or a human CD8 stalk or the mouse CD8 stalk. The spacer may alternatively comprise an alternative linker sequence which has similar length and/or domain spacing properties as an IgG1 Fc region, an IgG1 hinge or a CD8 stalk. A human IgG1 spacer may be altered to remove Fc binding motifs.

Examples of amino acid sequences for these spacers are given below:

```
SEQ ID NO: 15 (hinge-CH2CH3 of human IgG1)
AEPKSPDKTHTCPPCPAPPVAGPSVFLFPPKPKDTLMIARTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGKKD

SEQ ID NO: 16 (human CD8 stalk):
TTTPAPRPPTPAPTIASQPLSLRPEACRPAAGGAVHTRGLDFACDI

SEQ ID NO: 17 (human IgG1 hinge):
AEPKSPDKTHTCPPCPKDPK

SEQ ID NO: 18 (CD2 ectodomain)
KEITNALETVVGALGQDINLDIPSFQMSDDIDDIKWEKTSDKKKIAQFRK

EKETFKEKDTYKLFKNGTLKIKHLKTDDQDIYKVSIYDTKGKNVLEKIFD

LKIQERVSKPKISVVTCINTTLTCEVIVINGTDPELNLYQDGKHLKLSQR

VITHKVVTTSLSAKFKCTAGNKVSKESSVEPVSCPEKGLD

SEQ ID NO: 19 (CD34 ectodomain)
SLDNNGTATPELPTQGTFSNVSTNVSYQETTTPSTLGSTSLHPVSQH

GNEATTNITETTVKFTSTSVITSVYGNTNSSVQSQTSVISTVFTTPANVS

TPETTLKPSLSPGNVSDLSTTSTSLATSPTKPYTSSSPILSDIKAEIKCS

GIREVKLTQGICLEQNKTSSCAEFKKDRGEGLARVLCGEEQADADAGAQV

CSLLLAQSEVRPQCLLLVLANRTEISSKLQLMKKHQSDLKKLGILDFTEQ

DVASHQSYSQKT
```

Receptor Component Comprising a Plurality of First Binding Domains

The receptor component may comprise a plurality of first binding domains and thus be capable of recruiting more than one signalling component.

The plurality of first binding domains may be present in a single intracellular domain of the receptor component.

The receptor component may comprise an appropriate number of transmembrane domains such that each first binding domain is orientated on the intracellular side of the cell membrane. For example the receptor component may comprise 3, 5, 7, 9, 11, or more transmembrane domains. In this way, a single receptor component may recruit multiple signalling components amplifying signalling in response to antigen.

The first binding domains may each be variants which have a different affinity for the second binding domain of the signalling component.

Multiple Receptor Components

Figure 11:
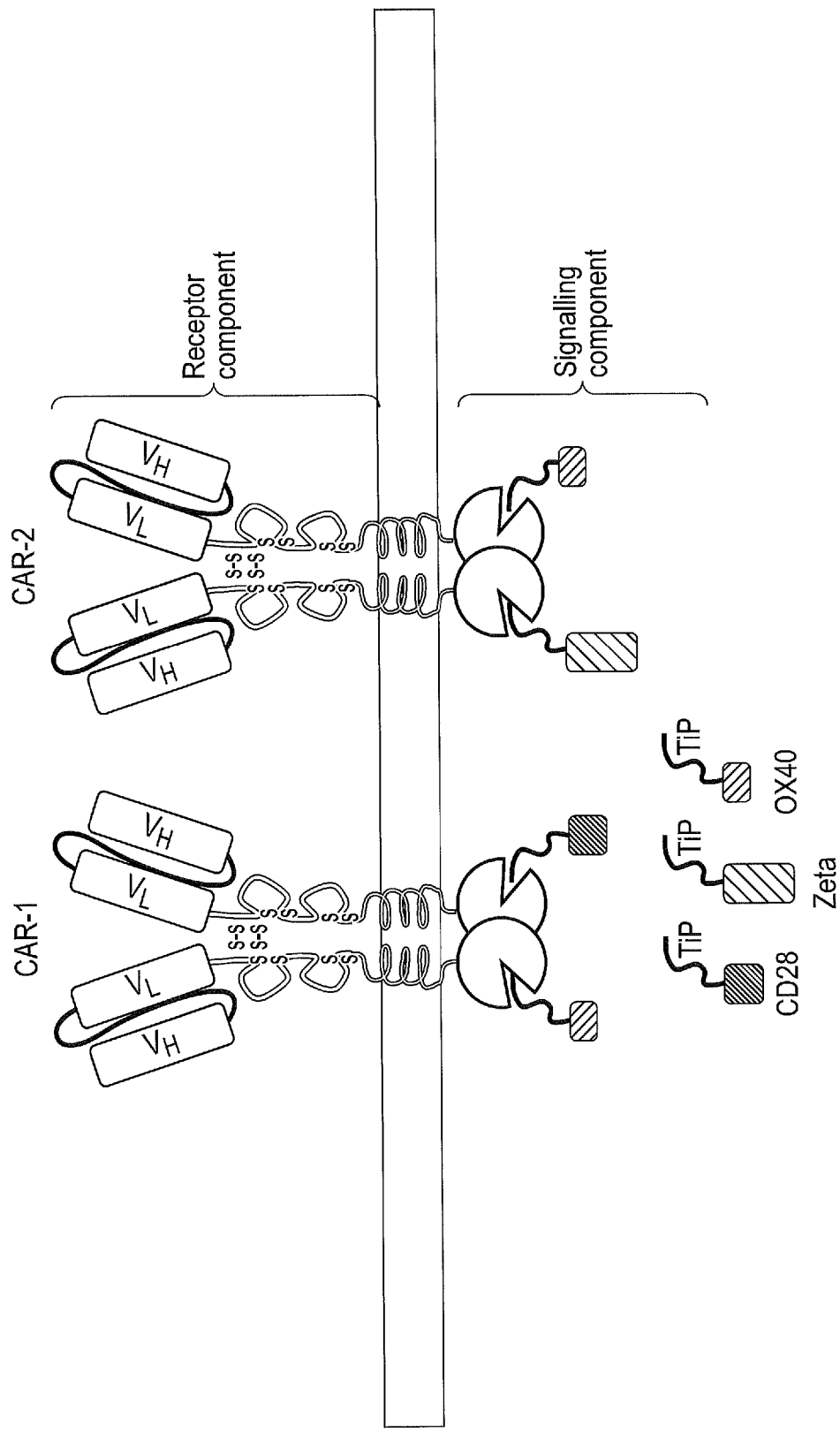
FIG. 11—A tetCAR signalling system utilising a plurality of receptor components and a plurality of signalling components, each signalling component containing a single endodomain.
Figure 12:
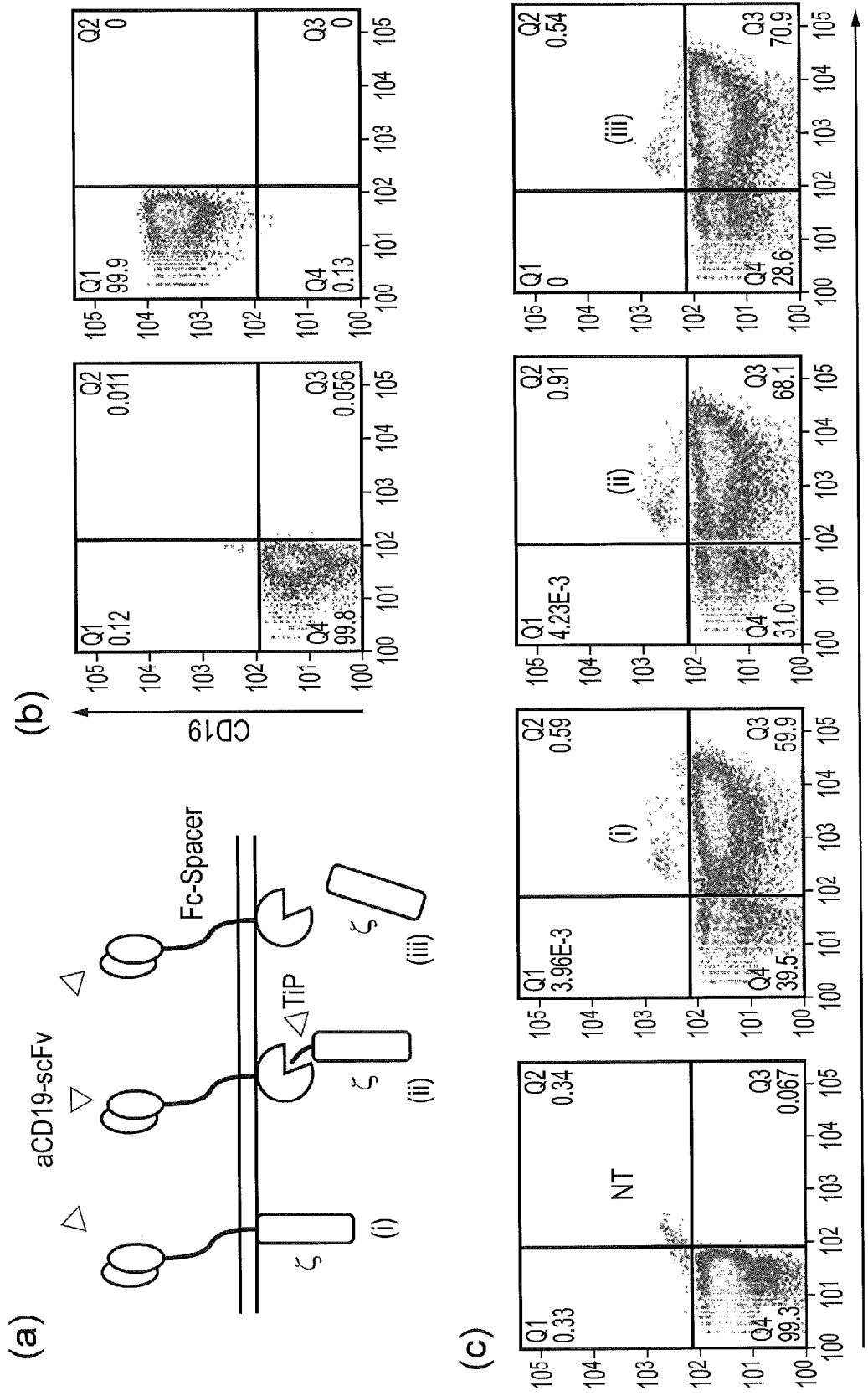
FIG. 12—TetCAR signalling in primary cells (a) Different constructs tested: (i) Classic CAR; (ii) tetCAR; (iii) control tetCAR where TiP has been deleted. (b) non-transduced and SupT1.CD19 cells stained for CD19; (c) Non-transduced T-cells and T-cells transduced with the different CAR constructs stained with anti-Fc.

In another embodiment of the invention, the CAR system may comprise two or more receptor components each recognizing different antigens but comprising of the same intracellular first binding domain. Such a CAR system would be capable of recognizing multiple antigens (FIG. 11). This might be useful for instance in avoiding tumour escape. In a further related aspect of the invention, the first binding domains of the receptor components differ in residues which dictate their affinity for the second binding domain of the signalling component. In this way, a CAR system can be tuned such that signalling in response to one antigen is greater or lesser than the response to another (FIG. 11). This might be useful for instance when targeting two tumour antigens simultaneously but one is expressed at a higher density than the other. Response to this antigen could be tuned down to avoid toxicity caused by over-stimulation.

Methods suitable for altering the amino acid residues of the first or second binding domain such that the binding affinity between the two domains is altered are known in the art and include substitution, addition and removal of amino acids using both targeted and random mutagenesis. Methods for determining the binding affinity between a first binding domain and a second binding domain are also well known in the art and include bioinformatics prediction of protein-protein interactions, affinity electrophoresis, surface plasma resonance, bio-layer interferometry, dual polarisation interferometry, static light scattering and dynamic light scattering.

Signalling Component

The present invention also provides a signalling component comprising a signalling domain and a second binding domain. The signalling component is a soluble molecule and thus localises to the cytoplasm when it is expressed in a cell, for example a T cell.

No signalling occurs through the signalling domain of the signalling component unless it is co-localised with the receptor component provided by the present invention. Such co-localisation occurs only in the absence of the agent, as described above.

Intracellular Signalling Domain

The intracellular signalling domain is the signal-transmission portion of a classical CAR. In the signalling system of the present invention the intracellular signalling domain (signalling domain) is located in the signalling component. In the absence of the agent, the membrane-bound, receptor component and the intracellular signalling component are brought into proximity. After antigen recognition, receptors cluster, native CD45 and CD148 are excluded from the synapse and a signal is transmitted to the cell.

As such the signalling domain of the signalling component is analogous to the endodomain of a classical CAR molecule.

The most commonly used signalling domain component is that of CD3-zeta endodomain, which contains 3 ITAMs. This transmits an activation signal to the T cell after antigen is bound. CD3-zeta may not provide a fully competent activation signal and additional co-stimulatory signalling may be needed. For example, chimeric CD28 and OX40 can be used with CD3-Zeta to transmit a proliferative/survival signal, or all three can be used together (illustrated in FIG. 1B).

Figure 3:
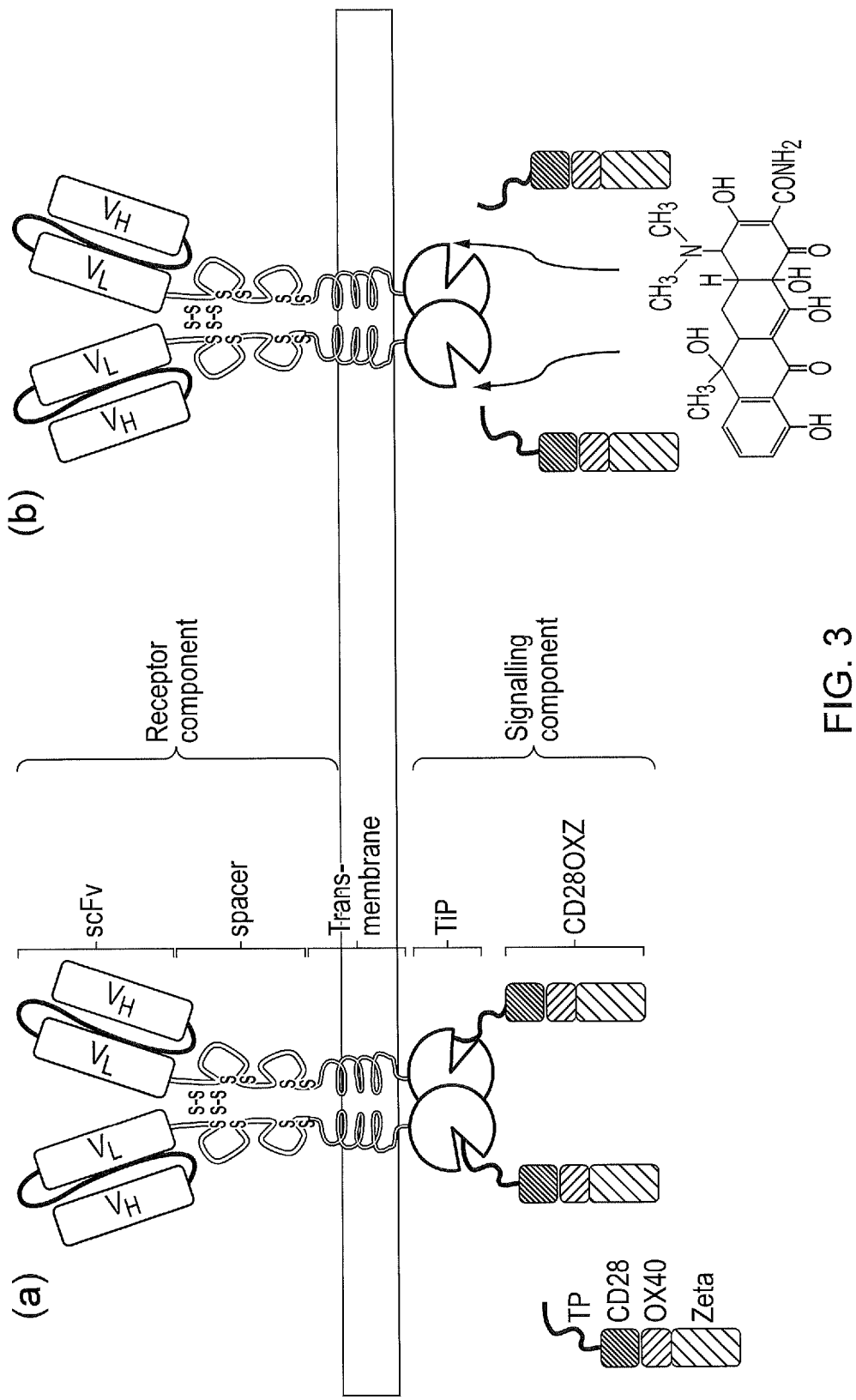
FIG. 3—(a) A membrane spanning receptor component comprises an extracellular antigen-binding domain, a trans-membrane domain and an intracellular linker to TetR. A separate molecule, the signalling component, comprises an intracellular protein which is generated by fusion of TiP to one or several T-cell signalling domains. In the absence of tetracycline or tetracycline analogues, the receptor and the signalling components interact and in the presence of cognate antigen the system signals. (b) In the presence of tetracycline or tetracycline analogues, TiP is displaced from TetR and the receptor can not transmit signals even in the presence of cognate antigen.
Figure 4:
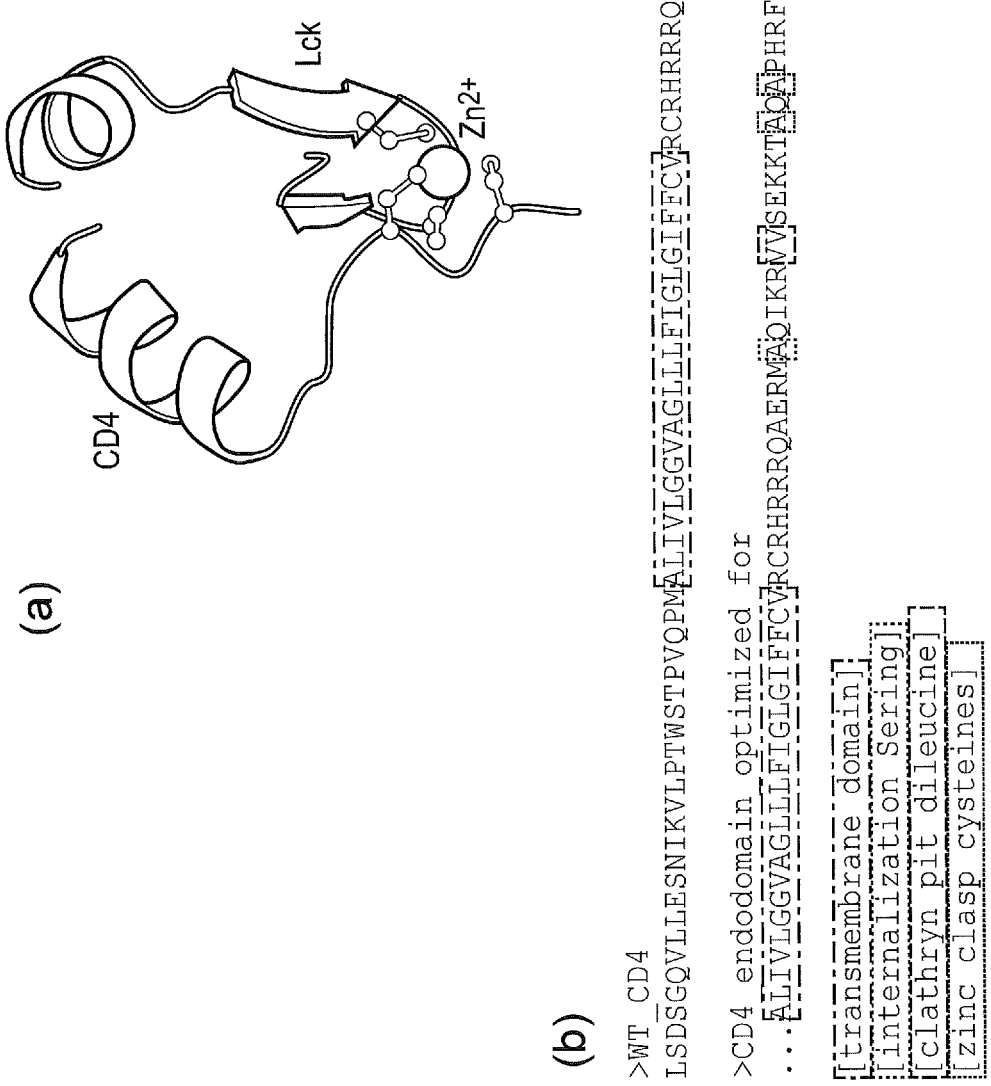
FIG. 4—(a) Intracellular linker domain derived from CD4. (b) Wildtype (WT) CD4 (SEQ ID NO: 28); CD4 endodomain (SEQ ID NO: 3).

The signalling component described herein comprises a signalling domain, it may comprise the CD3-Zeta endodomain alone, the CD3-Zeta endodomain with that of either CD28 or OX40 or the CD28 endodomain and OX40 and CD3-Zeta endodomain (FIG. 3A).

The signalling component of a CAR system according to the present invention may comprise the sequence shown as SEQ ID NO: 20, 21 or 22 or a variant thereof having at least 80% sequence identity.

```
SEQ ID NO: 20-CD3 Z endodomain
RVKFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDTYD

ALHMQALPPR

SEQ ID NO: 21-CD28 and CD3 Zeta endodomains
SKRSRLLHSDYMNMTPRRPGPTRKHYQPYAPPRDFAAYRSRVKFSRSADAP

AYQQGQNQLYNELNLGRREEYDVLDKRRGRDPEMGGKPRRKNPQEGLYNEL

QKDKMAEAYSEIGMKGERRRGKGHDGLYQGLSTATKDTYDALHMQALPPR

SEQ ID NO: 22-CD28, OX40 and CD3 Zeta endodomains
SKRSRLLHSDYMNMTPRRPGPTRKHYQPYAPPRDFAAYRSRDQRLPPDAHK

PPGGGSFRTPIQEEQADAHSTLAKIRVKFSRSADAPAYQQGQNQLYNELNL

GRREEYDVLDKRRGRDPEMGGKPRRKNPQEGLYNELQKDKMAEAYSEIGMK

GERRRGKGHDGLYQGLSTATKDTYDALHMQALPPR
```

A variant sequence may have at least 80%, 85%, 90%, 95%, 98% or 99% sequence identity to SEQ ID NO: 20, 21 or 22, provided that the sequence provides an effective intracellular signalling domain.

Multiple Signalling Components

Figure 9:
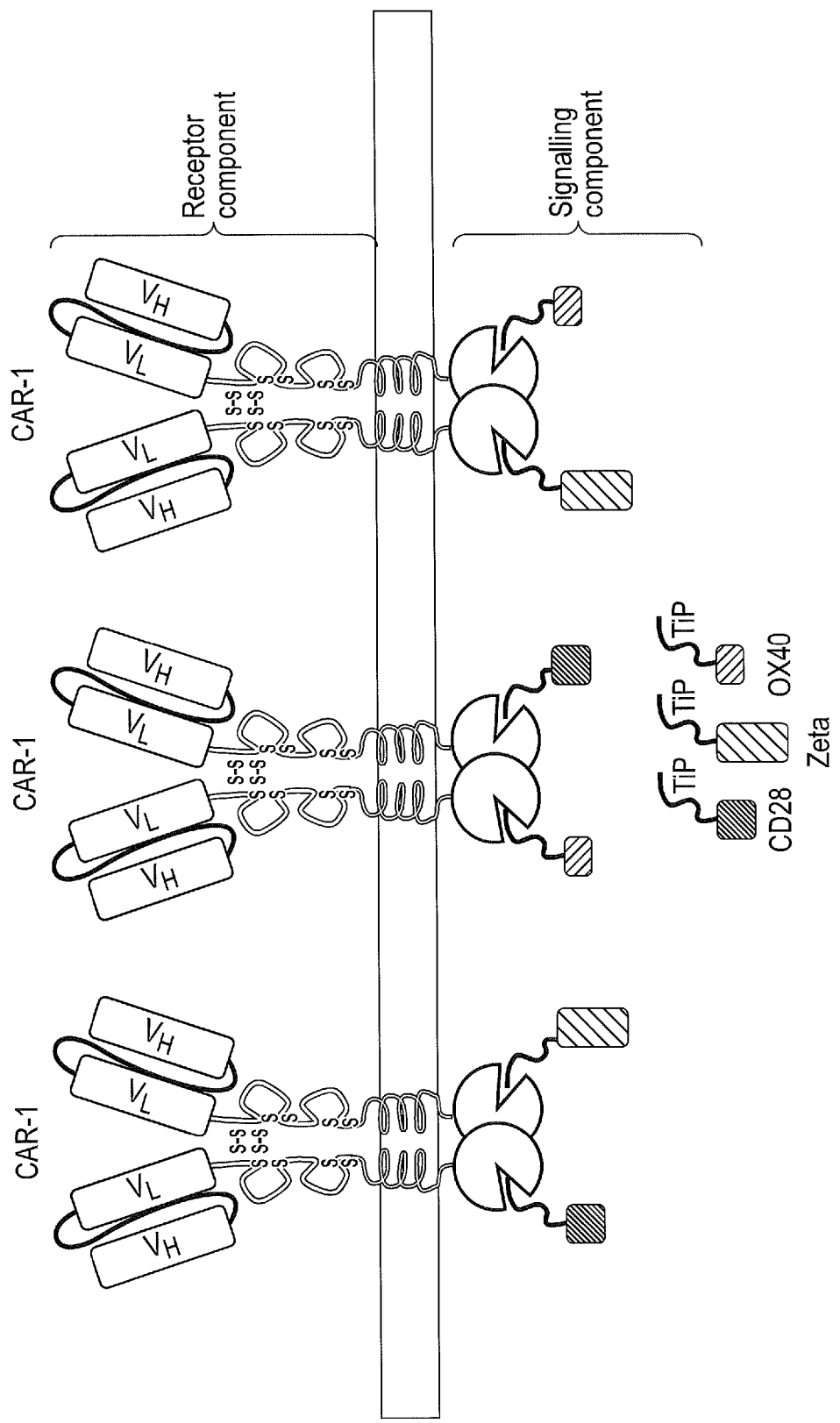
FIG. 9—A tetCAR signalling system utilising a plurality of signalling components containing single endodomains. A single CAR is expressed with many different signalling components all of which comprise TiP at their amino terminus but a different individual signalling domain, in contrast to a compound signalling domain. These randomly interact with the receptor component. Lack of steric interaction between the different signalling domains and their second messengers improves their function.

The signalling system according to the first aspect of the present invention may comprise a plurality of signalling components, each comprising a signalling domain and a second binding domain, wherein each second binding domain is bound by the same first binding domain of the receptor component but the signalling domains comprise different endodomains (FIG. 9). In this way, multiple different endodomains can be activated simultaneously. This is advantageous over a compound signalling domain since each signalling domain remains unencumbered from other signalling domains.

Figure 10:
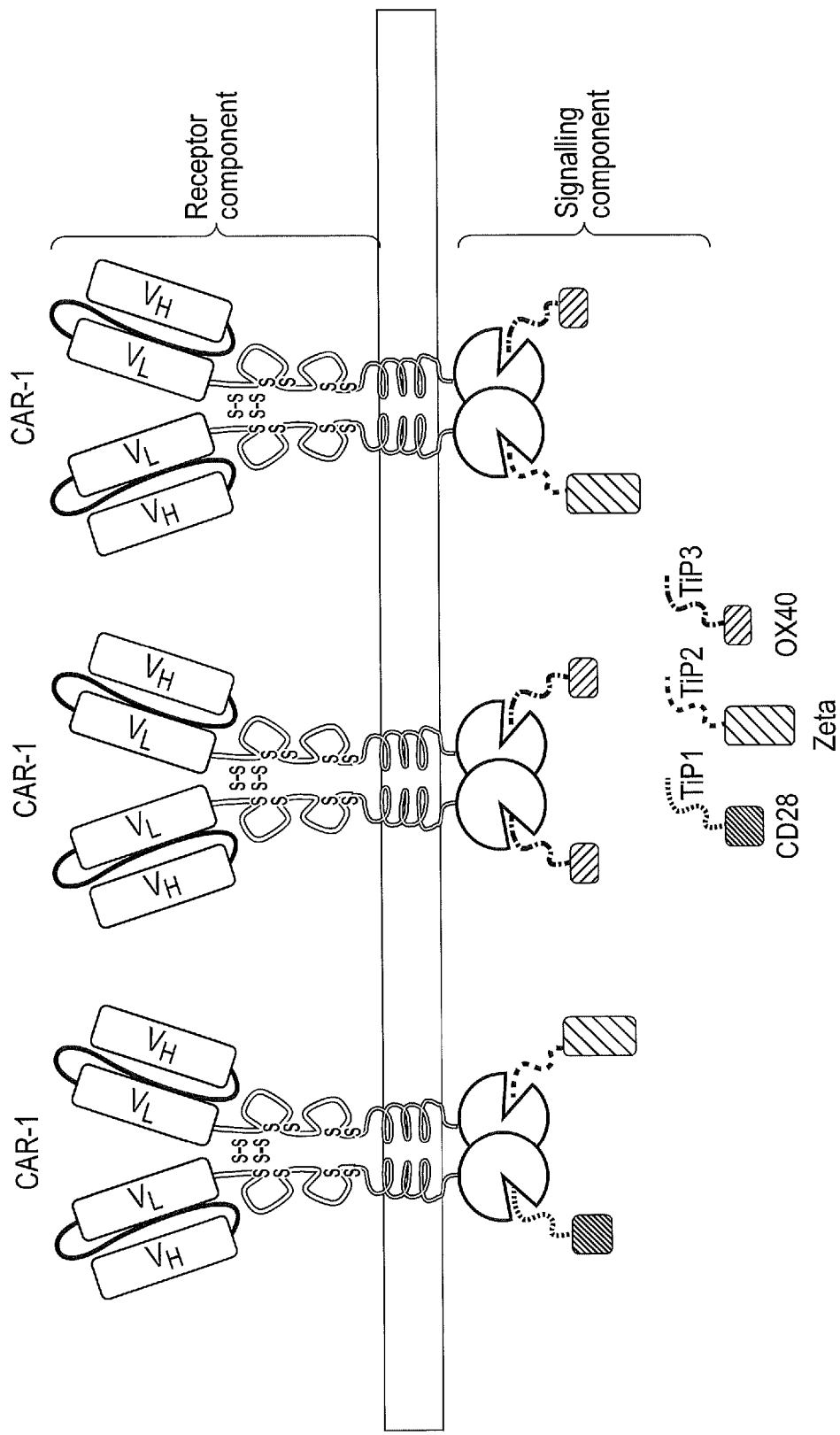
FIG. 10—A tetCAR signalling system utilising a plurality of signalling components containing single endodomains and different TiP domains. Each signalling component comprises of an individual signalling domain. Each signalling component also comprises of a TiP, however each TiP has different affinities to the TetR domain. Hence the stoichiometry of the interactions between the CAR and the signalling domains can be varied. In the example shown, the signalling system is constructed such that OX40>CD3Zeta>CD28.

If each signalling component comprises a second binding domain which differs in residues which alter their affinity to the first binding domain of the receptor component, the signalling components comprising different signalling domains ligate to the first binding domain with differing kinetics (FIG. 10). This allows greater control over the signalling in response to antigen-binding by the receptor component as different signalling components are recruited to the receptor component in varying kinetics/dynamics. This is advantageous since rather than a fixed equal ratio of signal transmitted by a compound endodomain, an optimal T-cell activation signal may require different proportions of different immunological signals.

Nucleic Acid

The present invention further provides a nucleic acid encoding the receptor component of the second aspect and a nucleic acid encoding a signalling component of the third aspect.

As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

The nucleic acid of the invention may be a nucleic acid which encodes both the receptor component and the signalling component.

The nucleic acid may produce a polypeptide which comprises the receptor component and the signalling component joined by a cleavage site. The cleavage site may be self-cleaving, such that when the polypeptide is produced, it is immediately cleaved into the receptor component and the signalling component without the need for any external cleavage activity.

Various self-cleaving sites are known, including the Foot-and-Mouth disease virus (FMDV) 2a self-cleaving peptide, which has the sequence shown:

```
                              SEQ ID NO: 23
          RAEGRGSLLTCGDVEENPGP.
          or
                              SEQ ID NO: 24
          QCTNYALLKLAGDVESNPGP
```

The nucleic acid may produce a polypeptide which comprises the sequence shown as SEQ ID NO: 25.

```
                                                SEQ ID NO: 25
MWTWNAYAFAAPSGGGSADAPAYQQGQNQLYNELNLGRREEYDVLDKRR

GRDPEMGGKPRRKNPQEGLYNELQKDKMAEAYSEIGMKGERRRGKGHDG

LYQGLSTATKDTYDALHMQALPPRRAEGRGSLLTCGDVEENPGPMAVPT

QVLGLLLLWLTDARCDIQMTQSPSSLSASVGDRVTITCRASEDIYFNLV

WYQQKPGKAPKLLIYDTNRLADGVPSRFSGSGSGTQYTLTISSLQPEDF

ATYYCQHYKNYPLTFGQGTKLEIKRSGGGGSGGGGSGGGGSGGGGSRSE

VQLVESGGGLVQPGGSLRLSGAASGFTLSNYGMHWIRQAPGKGLEWVSS

ISLNGGSTYYRDSVKGRFTISRDNAKSTLYLQMNSLRAEDTAVYYCAAQ

DAYTGGYFDYWGQGTLVTVSSMDPAEPKSPDKTHTCPPCPAPPVAGPSV

FLFPPKPKDTLMIARTPEVTCVVVDVSHEDPEVKFNWYVDGVEVHNAKT

KPREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQP
```

-continued

ENNYKTTPPVLDSDGSFFLYSKLTVDKSRWQQGNVFSCSVMHEALHNHY

TQKSLSLSPGKKDPM......SGGGGSMSRLDKSKVINSALELLNEVGI

EGLTTRKLAQKLGVEQPTLYWHVKNKRALLDALAIEMLDRHHTHFCPLE

GESWQDFLRNNAKSFRCALLSHRDGAKVHLGTRPTEKQYETLENQLAFL

CQQGFSLENALYALSAVGHFTLGCVLEDQEHQVAKEERETPTTDSMPPL

LRQAIELFDHQGAEPAFLFGLELIICGLEKQLKCESGS

Wherein . . . indicates the position where an antigen binding domain sequence may be included. Any antigen binding domain may be included, for example an scFV, as described herein.

The co-expressing sequence may be an internal ribosome entry sequence (IRES). The co-expressing sequence may be an internal promoter.

The present invention also provides a kit comprising a nucleic acid encoding the receptor component of the second aspect and/or a nucleic acid encoding a signalling component of the third aspect.

Vector

The present invention also provides a vector, or kit of vectors which comprises one or more nucleic acid sequence(s) encoding a receptor component of the second aspect and/or signalling component of the third aspect of the invention. Such a vector may be used to introduce the nucleic acid sequence(s) into a host cell so that it expresses the receptor component and signalling component of the CAR system according to the first aspect of the invention.

The vector may, for example, be a plasmid or a viral vector, such as a retroviral vector or a lentiviral vector, or a transposon based vector or synthetic mRNA.

The vector may be capable of transfecting or transducing a T cell or a NK cell.

Cytolytic Immune Cell

The present invention also relates to an immune cell comprising the CAR system according to the first aspect of the invention.

The cytolytic immune cell may comprise a nucleic acid or a vector of the present invention.

The cytolytic immune cell may comprise a receptor component and a signalling component of the present invention.

The cytolytic immune cell may comprise at least one signalling component of the present invention. For example the cytolytic immune cell may comprise one, two, three, four, five, up to a plurality of signalling components of the present invention.

The cytolytic immune cell may comprise at least one receptor component of the present invention. For example the cytolytic immune cell may comprise one, two, three, four, five, up to a plurality of receptor components of the present invention.

Cytolytic immune cells can be T cells or T lymphocytes which are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytolytic T cells (TC cells, or CTLs) destroy virally infected cells and tumor cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+ CD25+ FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

Natural Killer Cells (or NK cells) are a type of cytolytic cell which form part of the innate immune system. NK cells provide rapid responses to innate signals from virally infected cells in an MHC independent manner NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The CAR cells of the invention may be any of the cell types mentioned above.

T or NK cells expressing the molecules of the CAR system according to the first aspect of the invention may either be created ex vivo either from a patient's own peripheral blood (1st party), or in the setting of a haematopoietic stem cell transplant from donor peripheral blood (2nd party), or peripheral blood from an unconnected donor (3rd party).

Alternatively, T or NK cells expressing the molecules of the CAR system according to the first aspect of the invention may be derived from ex vivo differentiation of inducible progenitor cells or embryonic progenitor cells to T cells. Alternatively, an immortalized T-cell line which retains its lytic function and could act as a therapeutic may be used.

In all these embodiments, CAR cells are generated by introducing DNA or RNA coding for the receptor component and signalling component by one of many means including transduction with a viral vector, transfection with DNA or RNA.

The CAR cell of the invention may be an ex vivo T or NK cell from a subject. The T or NK cell may be from a peripheral blood mononuclear cell (PBMC) sample. T or NK cells may be activated and/or expanded prior to being transduced with nucleic acid encoding the molecules providing the CAR system according to the first aspect of the invention, for example by treatment with an anti-CD3 monoclonal antibody.

The T or NK cell of the invention may be made by:
(i) isolation of a T or NK cell-containing sample from a subject or other sources listed above; and
(ii) transduction or transfection of the T or NK cells with one or more a nucleic acid sequence(s) encoding the receptor component and/or signalling component of the CAR system according to the second and third aspects of the invention.

The T or NK cells may then by purified, for example, selected on the basis of expression of the antigen-binding domain of the antigen-binding polypeptide.

The present invention also provides a kit which comprises a T or NK cell comprising the CAR system according to the first aspect of the invention.

Pharmaceutical Composition

The present invention also relates to a pharmaceutical composition containing a plurality of cytolytic immune cells expressing the components of the CAR system of the first aspect of the invention. The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Method of Treatment

The present invention provides a method for treating and/or preventing a disease which comprises the step of administering the cytolytic immune cells of the present invention (for example in a pharmaceutical composition as described above) to a subject.

A method for treating a disease relates to the therapeutic use of the cytolytic immune cells of the present invention. Herein the cells may be administered to a subject having an existing disease or condition in order to lessen, reduce or improve at least one symptom associated with the disease and/or to slow down, reduce or block the progression of the disease.

The method for preventing a disease relates to the prophylactic use of the cytolytic immune cells of the present invention. Herein such cells may be administered to a subject who has not yet contracted the disease and/or who is not showing any symptoms of the disease to prevent or impair the cause of the disease or to reduce or prevent development of at least one symptom associated with the disease. The subject may have a predisposition for, or be thought to be at risk of developing, the disease.

The method may involve the steps of:
(i) isolating a T or NK cell-containing sample;
(ii) transducing or transfecting such cells with a nucleic acid sequence or vector provided by the present invention;
(iii) administering the cells from (ii) to a subject.

The T or NK cell-containing sample may be isolated from a subject or from other sources, for example as described above. The T or NK cells may be isolated from a subject's own peripheral blood (1st party), or in the setting of a haematopoietic stem cell transplant from donor peripheral blood (2nd party), or peripheral blood from an unconnected donor (3rd party).

The methods provided by the present invention for treating a disease may involve monitoring the progression of the disease and any toxic activity and administering an agent suitable for use in the CAR system according to the first aspect of the invention to inhibit CAR signalling and thereby reduce or lessen any adverse toxic effects.

The methods provided by the present invention for treating a disease may involve monitoring the progression of the disease and monitoring any toxic activity and adjusting the dose of the agent administered to the subject to provide acceptable levels of disease progression and toxic activity.

Monitoring the progression of the disease means to assess the symptoms associated with the disease over time to determine if they are reducing/improving or increasing/worsening.

Toxic activities relate to adverse effects caused by the CAR cells of the invention following their administration to a subject. Toxic activities may include, for example, immunological toxicity, biliary toxicity and respiratory distress syndrome.

The level of signalling through the signalling system of the first aspect of the invention, and therefore the level of activation of CAR cells expressing the signalling system, may be adjusted by altering the amount of agent present, or the amount of time the agent is present. In the present method the level of CAR cell activation may be augmented by decreasing the dose of agent administered to the subject or decreasing the frequency of its administration. Conversely, the level of CAR cell activation may be reduced by increasing the dose of the agent, or the frequency of administration to the subject.

Higher levels of CAR cell activation are likely to be associated with reduced disease progression but increased toxic activities, whilst lower levels of CAR cell activation are likely to be associated with increased disease progression but reduced toxic activities.

The present invention also provides a method for treating and/or preventing a disease in a subject which subject comprises cells of the invention, which method comprises the step of administering an agent suitable for use in the CAR system according to the first aspect to the subject. As such, this method involves administering a suitable agent to a subject which already comprises CAR cells of the present invention.

As such the dose of agent administered to a subject, or the frequency of administration, may be altered in order to provide an acceptable level of both disease progression and toxic activity. The specific level of disease progression and toxic activities determined to be 'acceptable' will vary according to the specific circumstances and should be assessed on such a basis. The present invention provides a method for altering the activation level of the CAR cells in order to achieve this appropriate level.

The agent may be administered in the form of a pharmaceutical composition. The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

The present invention provides a CAR cell of the present invention for use in treating and/or preventing a disease.

The invention also relates to the use of a CAR cell of the present invention in the manufacture of a medicament for the treatment and/or prevention of a disease.

The present invention also provides an agent suitable for inhibiting a CAR system according to the first aspect of the invention for use in treating and/or preventing a disease.

The present invention also provides an agent for use in inhibiting a CAR system according to the first aspect of the invention in a CAR cell.

The invention also provides the use of an agent suitable for inhibiting a CAR system according to the first aspect of the invention in the manufacture of a medicament for the treatment and/or prevention of a disease.

The disease to be treated and/or prevented by the methods of the present invention may be an infection, such as a viral infection.

The methods of the invention may also be for the control of pathogenic immune responses, for example in autoimmune diseases, allergies and graft-vs-host rejection.

The methods may be for the treatment of a cancerous disease, such as bladder cancer, breast cancer, colon cancer, endometrial cancer, kidney cancer (renal cell), leukaemia, lung cancer, melanoma, non-Hodgkin lymphoma, pancreatic cancer, prostate cancer and thyroid cancer.

The CAR cells of the present invention may be capable of killing target cells, such as cancer cells. The target cell may be recognisable by expression of a TAA, for example the expression of a TAA provided above in Table 1.

The CAR cells and pharmaceutical compositions of present invention may be for use in the treatment and/or prevention of the diseases described above.

The CAR cells and pharmaceutical compositions of present invention may be for use in any of the methods described above.

The invention will now be further described by way of Examples, which are meant to serve to assist one of ordinary skill in the art in carrying out the invention and are not intended in any way to limit the scope of the invention.

EXAMPLES

Example 1—Functionality of the TetCAR Signalling System

Figure 5:
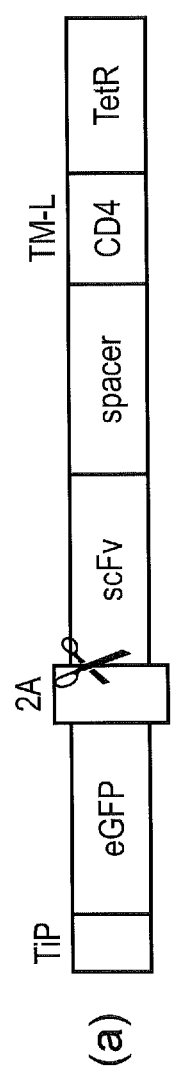
FIG. 5—Test construct with eGFP to demonstrate function of the system. (a) a bicistronic construct expressed as a single transcript which self-cleaves at the 2A site to yield: TiP fused to eGFP; and a CAR with TetR as its endodomain. (b) Fluorescent micrograph of SupT1 cells expressing this construct in the absence of tetracycline. The eGFP fluorescence can clearly be seen at the cell membrane; (c) Fluorescent micrograph of the same cells but now in the presence of tetracycline. Here, the eGFP is cytoplasmic showing that tetracycline has displaced TiP.
Figure 5:
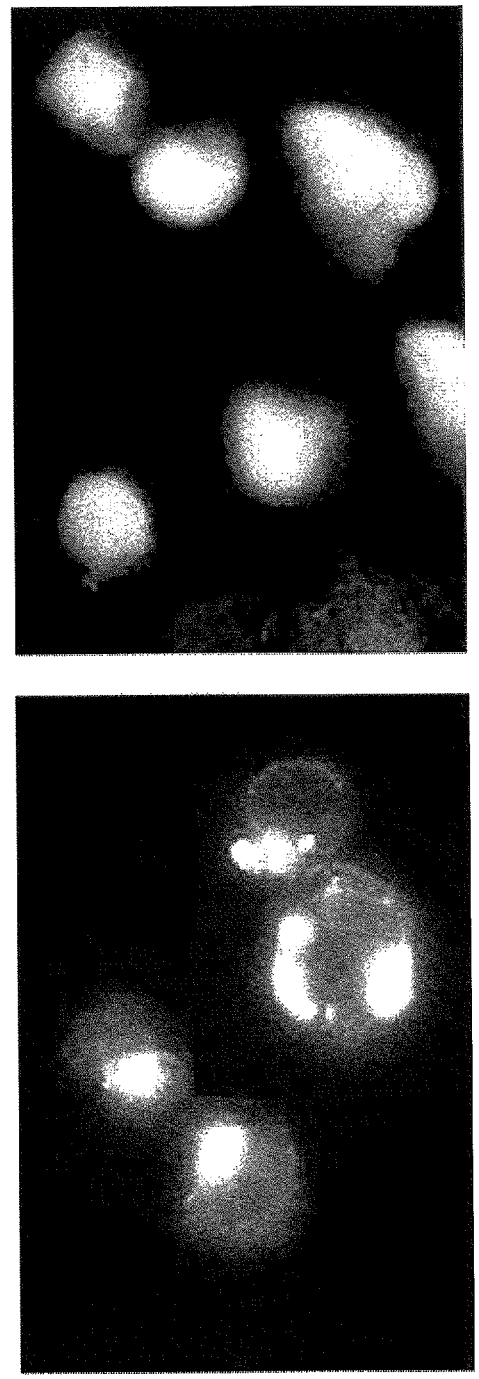

A bicistronic construct was expressed as a single transcript which self-cleaves at the 2A site to yield TiP fused to eGFP and a CAR with TetR as its endodomain (FIG. 5a).

Fluorescent microscopy of SupT1 cells expressing this construct in the absence of tetracycline demonstrated that eGFP fluorescence can clearly be seen at the cell membrane (FIG. 5b); whilst in the presence of tetracycline the eGFP was cytoplasmic (FIG. 5c). These data demonstrate that tetracycline has displaced TiP from the TetR CAR.

Example 2—Signalling Through the TetCAR System

Figure 6:
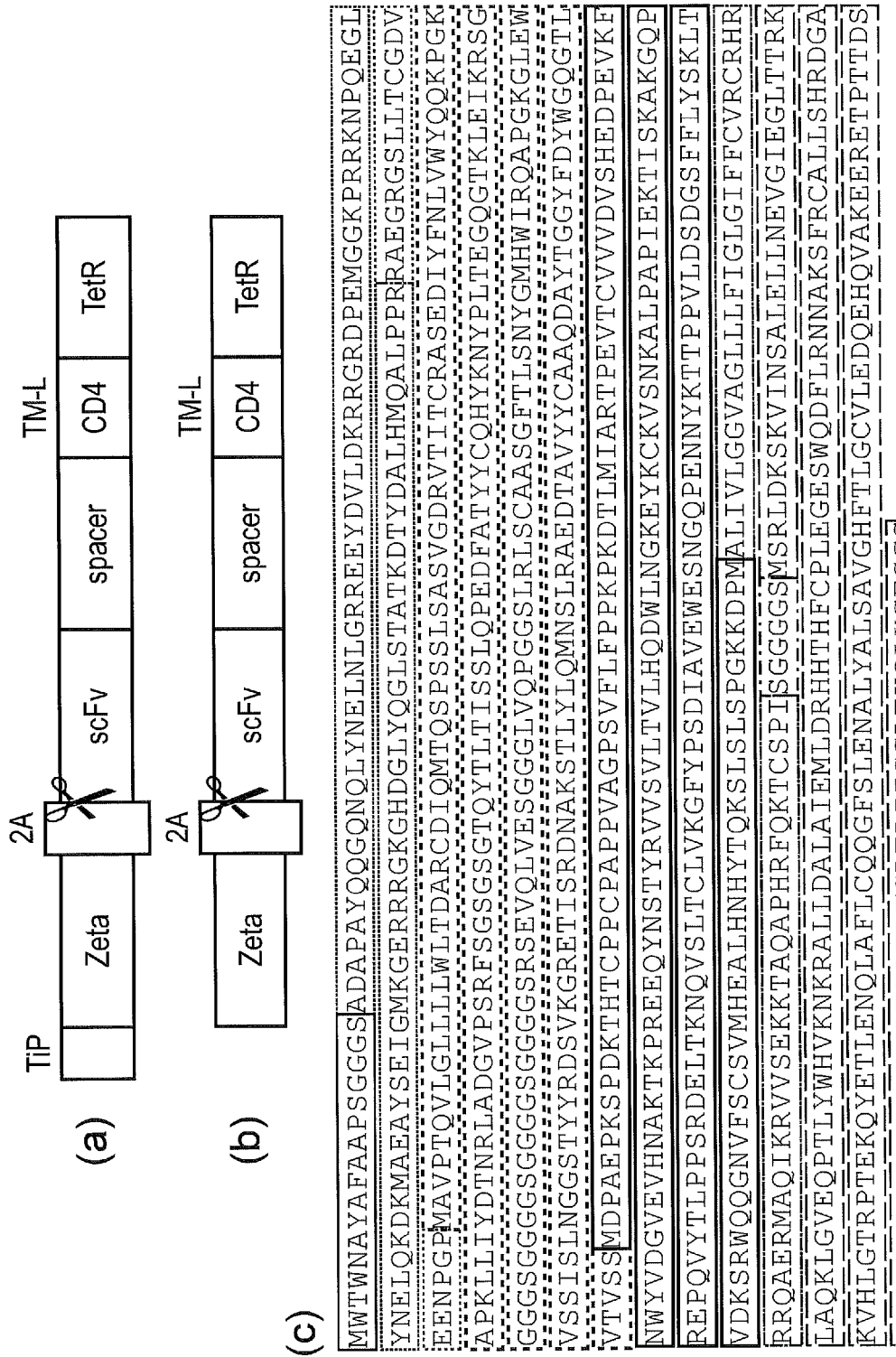
FIG. 6—Initial TetCAR construct and control (a) a bicistronic construct expressed as a single transcript which self-cleaves at the 2A site to yield: a signalling component which comprises TiP fused via a flexible linker to the endodomain of CD3-Zeta; and a receptor component which comprises a CD33 recognizing scFv, a spacer derived from the Fc domain of IgG1, a CD4 derived transmembrane and intracellular domain; and TetR. (b) a control was also constructed which was identical except TiP was absent from the signalling component. (c) annotated amino-acid sequence of the basic TetCAR is shown (SEQ ID NO: 29).

A bicistronic construct was expressed in BW5 T cells as a single transcript which self-cleaves at the 2A site to yield a signalling component which comprises TiP fused via a flexible linker to the endodomain of CD3-Zeta; and a receptor component which comprises a CD33 recognizing scFv, a spacer derived from the Fc domain of IgG1, a CD4 derived transmembrane and intracellular domain; and TetR (FIG. 6a). A control was also expressed which was identical except that TiP was absent from the signalling component (FIG. 6b).

Figure 7:
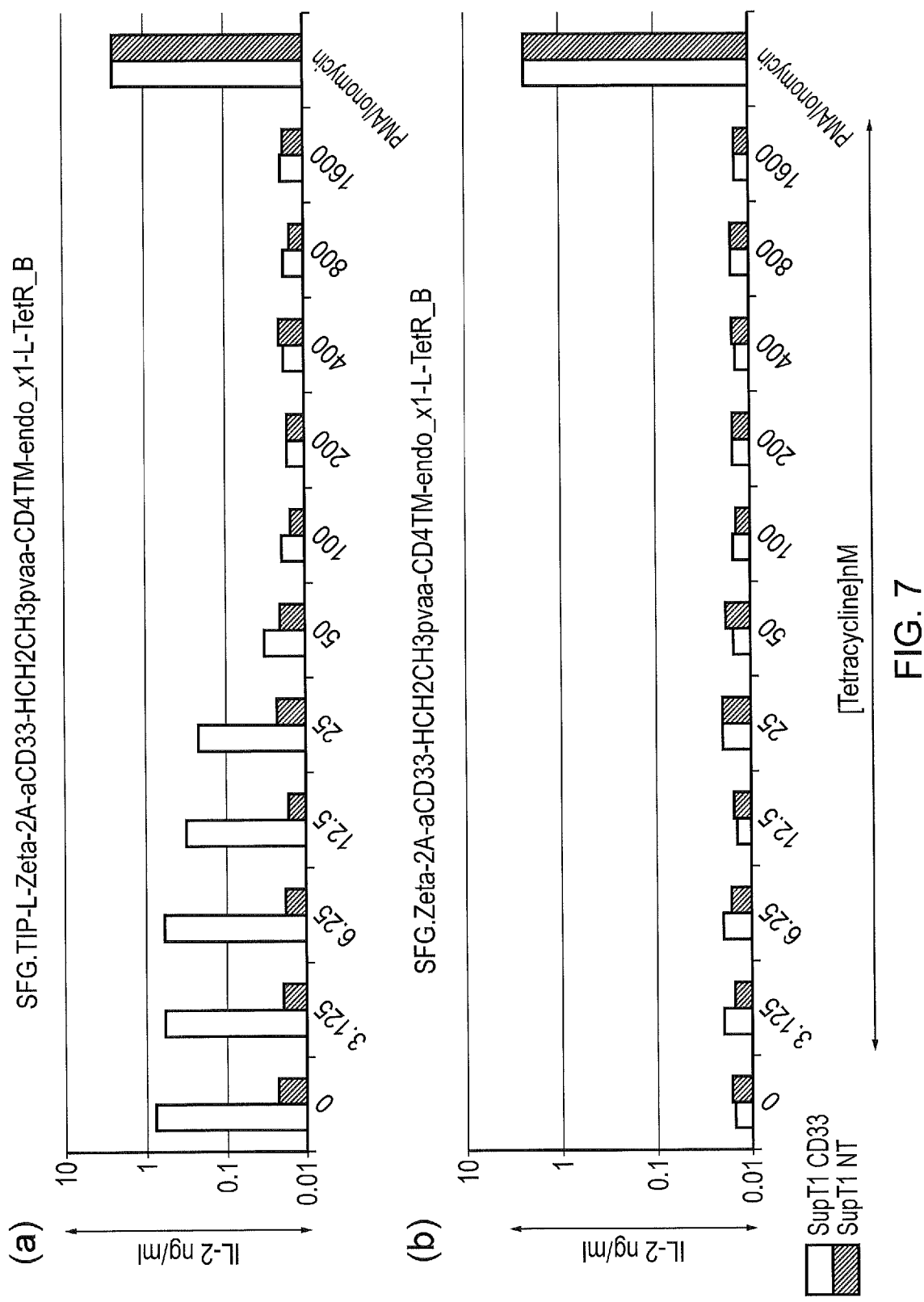
FIG. 7—Function of the initial TetR construct in comparison with control. (a) TetCAR was expressed in BW5 T-cells. These T-cells were challenged with wild-type SupT1 cells or SupT1 cells engineered to express CD33 in the absence of tetracycline or in the presence of increasing concentrations of tetracycline. T-cells challenged with wild-type SupT1 cells do not activate in either the presence or absence of Tetracyline; T-cells challenged with SupT1 cells expressing CD33 activate in the absence of Tetracycline, but activation is rapidly inhibited in the presence of tetracycline with activation fully inhibited in the presence of 100 nM of Tetracycline. (b) Control TetCAR which lacks the TiP domain was transduced into BW5. Once again, these T-cells were challenged with wild-type SupT1 cells or SupT1 cells engineered to express CD33 in the absence or in the presence of increasing concentration of Tetracycline. A lack of TiP element in the signalling component resulted in no signalling in any conditions.
Figure 8:
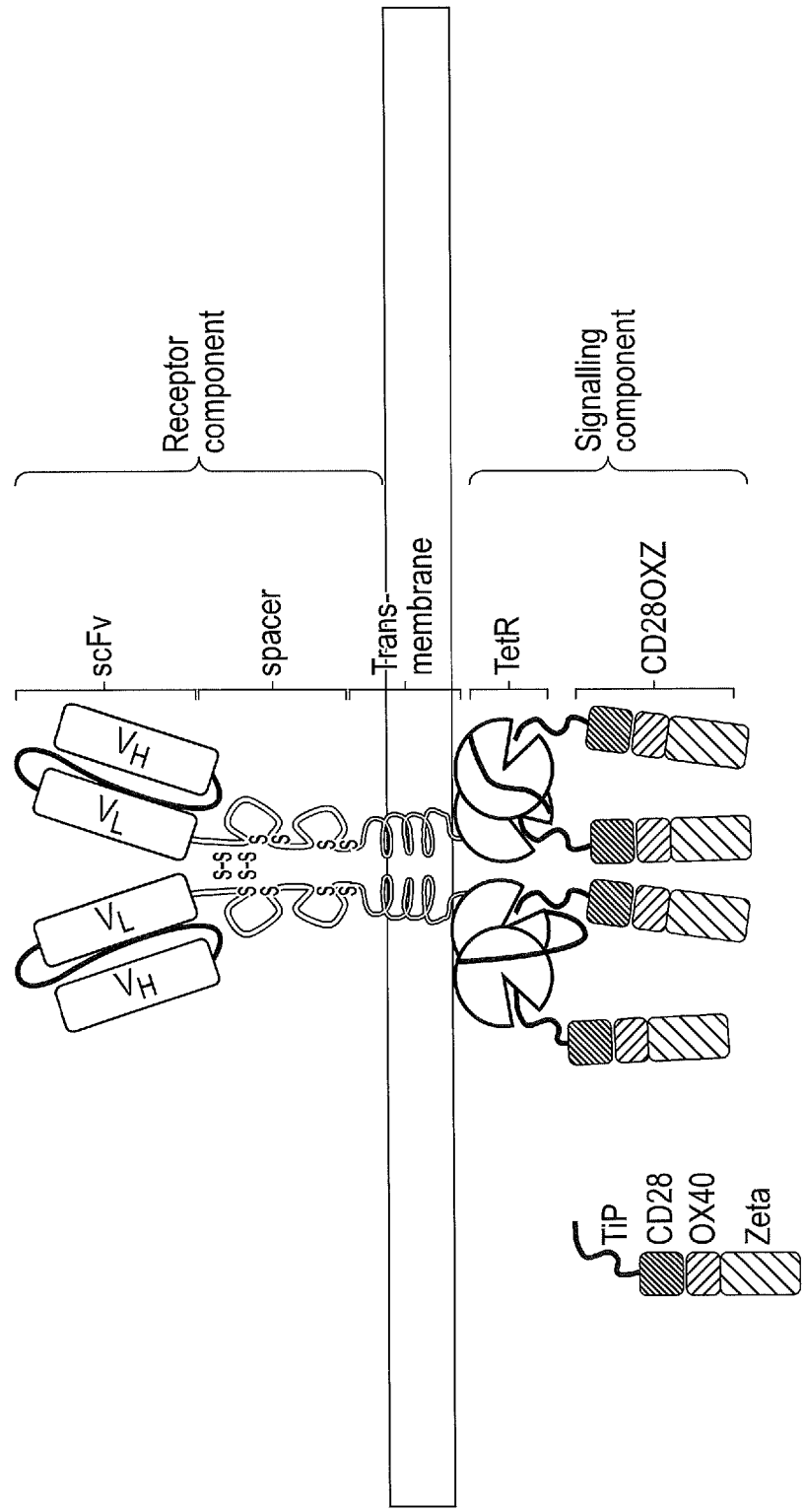
FIG. 8—Dual tetR domain tetCARs. tetR is expressed as a single-chain with two TetRs attached together. If tetR domains with differing affinity for tetracycline (and hence TiP) are used, the kinetics of Tetracycline mediated displacement of TiP can modulate the levels of signalling.

The BW5 T-cells were challenged with wild-type SupT1 cells or SupT1 cells engineered to express CD33 in the absence of tetracycline or in the presence of increasing concentrations of tetracycline. T-cells challenged with wild-type SupT1 cells did not activate in either the presence or absence of Tetracyline; T-cells challenged with SupT1 cells expressing CD33 were activated in the absence of Tetracycline, but activation is rapidly inhibited in the presence of tetracycline with activation fully inhibited in the presence of 100 nM of tetracycline (FIG. 7a).

Control TetCAR which lacks the TiP domain was also transduced into BW5. Once again, these T-cells were challenged with wild-type SupT1 cells or SupT1 cells engineered to express CD33 in the absence or in the presence of increasing concentration of Tetracycline. A lack of TiP element in signalling component resulted in no signalling in any conditions (FIG. 7b).

Example 3—Signalling of the TetCAR System in Primary T Cells

Figure 13:
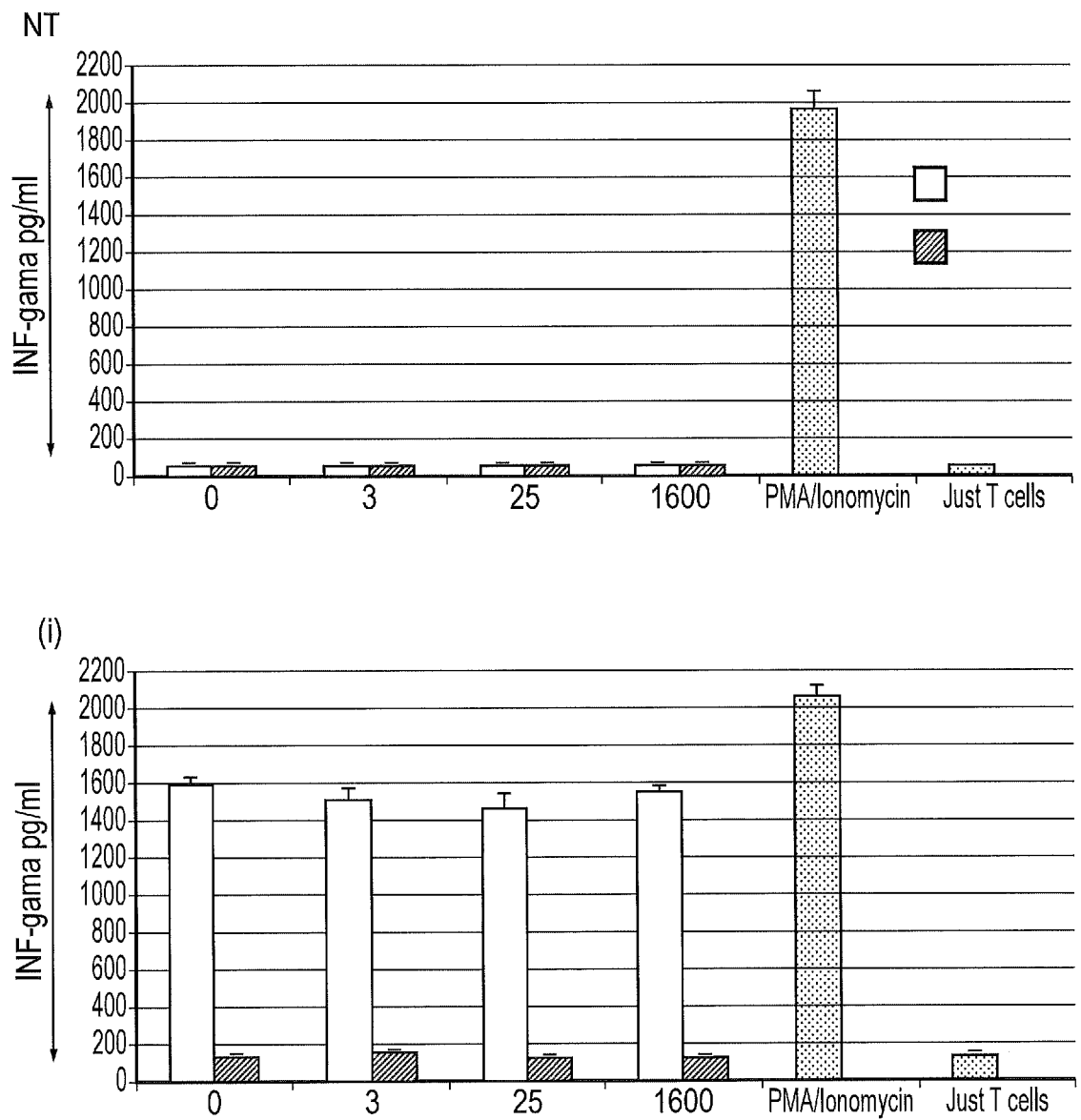
FIG. 13—Interferon-Gamma release from non-transduced T-cells, and T-cells transduced with the different CAR construct challenged ((i) Classical first generation CAR, (ii) tetCAR and (iii) control tetCAR), with SupT1 cells, SupT1.CD19 cells in different concentrations of Tetracyline.
Figure 13:
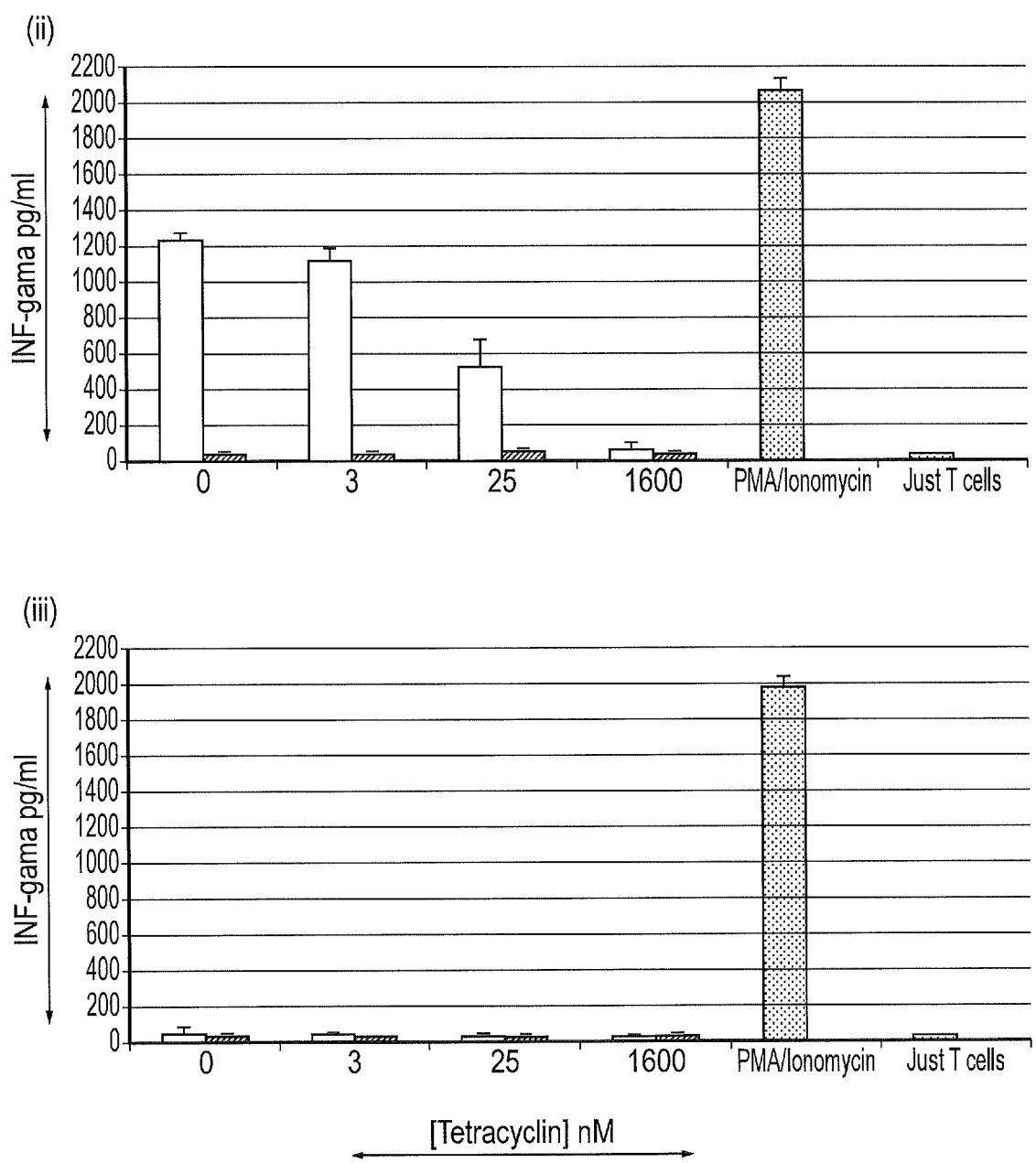

SupT1 cells (which are CD19 negative), were engineered to be CD19 positive giving target negative and positive cell lines which were as similar as possible. Primary human T-cells from 3 donors were transduced with three CAR constructs: (i) "Classical" 1st generation anti-CD19 CAR; (ii) 1st generation anti-CD19 tetCAR; (iii) Control anti-CD19 tetCAR where TiP is missing from endodomain. Non-transduced T-cells and T-cells transduced with the different CAR constructs were challenged 1:1 with either SupT1 cells or SupT1.CD19 cells in the presence of different concentrations of Tetracycline. Supernatant was sampled 48 hours after challenge. Supernatant from background (T-cells alone), and maximum (T-cells stimulated with PMA/Ionomycin) was also samples. Interferon-gamma was measured in supernatants by ELISA (FIG. 13). "Classical" CAR T-cells were activated by SupT1.CD19 irrespective of tetracycline. TetCAR T-cell were activated by SupT1.CD19 cells but activation was inhibited by Tetracycline. The control TetCAR and NT T-cells did not respond to SupT1.CD19 cells.

Example 4—Killing of Target Cells

Figure 14:
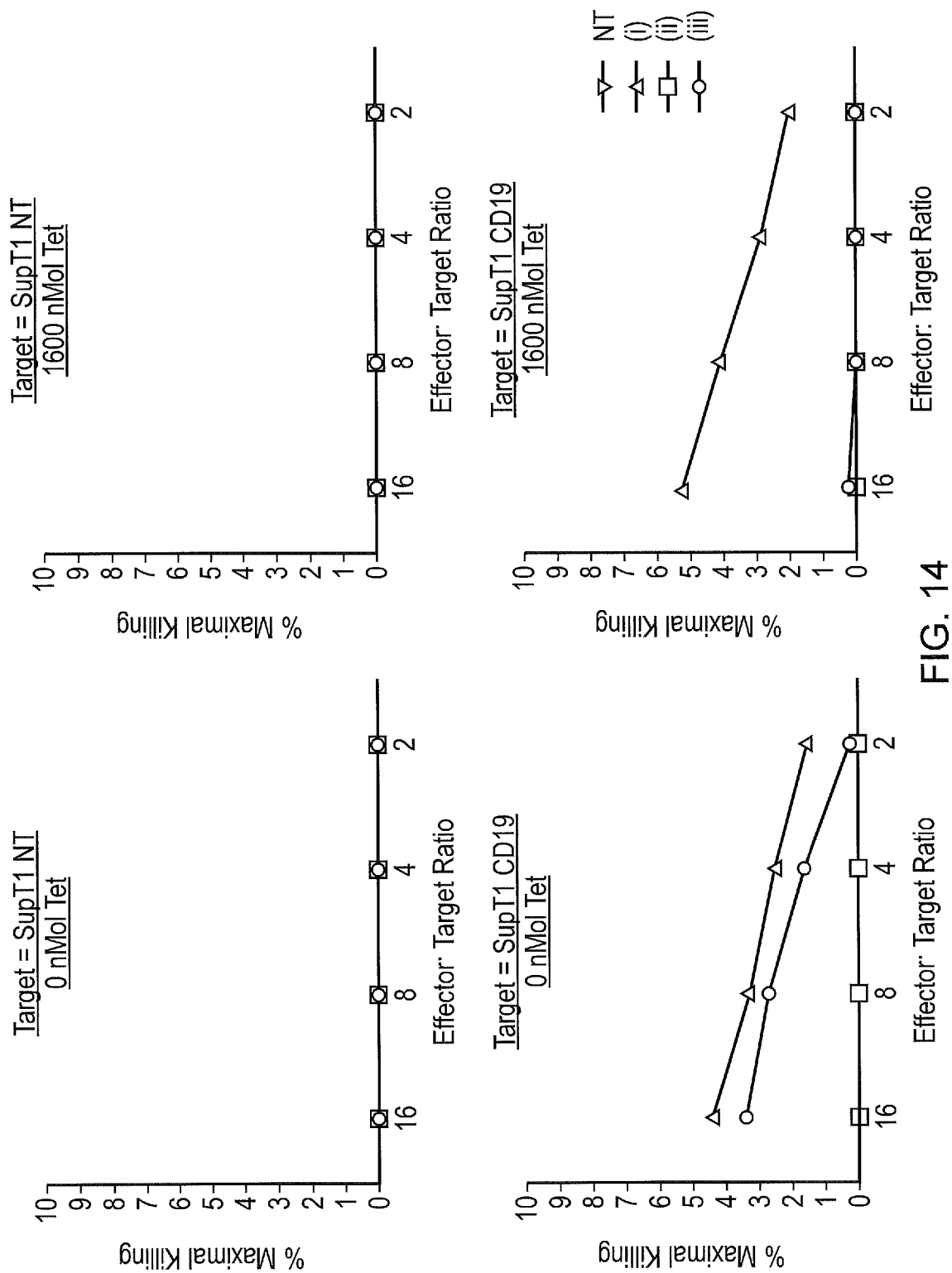
FIG. 14—Killing of target cells. A chromium release assay was used to demonstrate killing of target cells (SupT1.CD19) in the absence of tetracycline. Key: (i)—regular CAR; (ii)—tetCAR; (iii)—control tetCAR (no TiP on endodomain).

Following on from the interferon-gamma release study described in Example 3, killing of target cells was demonstrated using a chromium release assay. SupT1 and SupT1.CD19 cells were loaded with $^{51}$Cr and incubated with control and Tet-CAR T-cells for 4 hours in the presence or absence of tetracycline. Lysis of target cells was determined by counting $^{51}$Cr in the supernatant. The results are shown in FIG. 14. It was shown that Tet-CAR T-cells lysed SupT1.CD19 target cells only in the absence of Tetracycline.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cellular immunology or related fields are intended to be within the scope of the following claims.

The invention claimed is:

1. A chimeric antigen receptor (CAR) system comprising;
   (i) a receptor component comprising an extracellular antigen binding domain, a spacer, a transmembrane domain, and a first intracellular binding domain; and
   (ii) an intracellular signalling component comprising a signalling domain and a second binding domain which specifically binds to the first intracellular binding domain of the receptor component;
   wherein (i) and (ii) are separate molecules;
   wherein the receptor component and signaling component are co-expressed;
   wherein binding of the first and second binding domains of the CAR system is disruptable by the presence of an agent,
   wherein, in the absence of the agent, the receptor component and the intracellular signalling component heterodimerize, and binding of the antigen binding domain to antigen results in signalling through the signalling domain, whereas in the presence of the agent, the receptor component and the signalling component do not heterodimerize, and binding of the antigen binding domain to antigen does not result in signalling through the signalling domain; and wherein the first intracellular binding domain comprises Tet Repressor Protein (TetR) or a variant thereof and the second binding domain comprises Transcription inducing peptide (TiP) or a variant thereof; or wherein the first intracellular binding domain comprises TiP or a variant thereof and the second binding domain comprises TetR or a variant thereof; and the agent is tetracycline, doxycycline or minocycline or an analogue thereof.

2. The CAR system according to claim 1, wherein the signalling domain of the intracellular signalling component comprises a single endodomain selected from CD3 zeta endodomain, CD28 endodomain, 41 BB endodomain and OX40 endodomain.

3. The CAR system according to claim 1, wherein the signalling domain of the intracellular signalling component comprises at least one of CD3 zeta endodomain, CD28 endodomain, 41 BB endodomain and OX40 endodomain.

4. The CAR system according to claim 1, wherein the first binding domain comprises Tet Repressor Protein (TetR) and the second binding domain comprises Transcription inducing peptide (TiP).

5. The CAR system according to claim 1, wherein the first binding domain comprises TiP and the second binding domain comprises TetR.

6. A polynucleotide that comprises a nucleic acid sequence encoding a CAR signalling system,
wherein the CAR signalling system comprises:
 (i) a receptor component comprising an extracellular antigen binding domain, a spacer, a transmembrane domain, and a first intracellular binding domain; and
 (ii) an intracellular signalling component comprising a signalling domain and a second binding domain which specifically binds the first intracellular binding domain of the receptor component;
wherein the receptor component and signaling component are co-expressed;
wherein (i) and (ii) are separate molecules;
wherein binding of the first and second binding domains of the CAR system is disruptable by the presence of an agent,
wherein, in the absence of the agent, the receptor component and the intracellular signalling component heterodimerize, and binding of the antigen binding domain to antigen results in signalling through the signalling domain, whereas in the presence of the agent, the receptor component and the signalling component do not heterodimerize, and binding of the antigen binding domain to antigen does not result in signalling through the signalling domain;
wherein the first intracellular binding domain comprises Tet Repressor Protein (TetR) or a variant thereof and the second binding domain comprises Transcription inducing peptide (TiP) or a variant thereof; or wherein the first intracellular binding domain comprises TiP or a variant thereof and the second binding domain comprises TetR or a variant thereof; and the agent is tetracycline, doxycycline or minocycline or an analogue thereof; and
wherein the receptor component and signalling component are co-expressed, joined by a self-cleaving peptide which is cleaved between the receptor component and the signalling component after translation.

7. A vector comprising a polynucleotide according to claim 6.

8. A T cell or NK cell which expresses a CAR system according to claim 1.

9. A pharmaceutical composition comprising a plurality of T cells or NK cells that express the receptor component and the intracellular signalling component of the CAR system of claim 1.

10. A method for treating a subject, which comprises administering a pharmaceutical composition according to claim 9 to the subject.

11. A method for treating a subject comprising:
 (i) isolating of a T cell- or NK cell-containing sample;
 (ii) transducing or transfecting the T cells or NK cells with a polynucleotide according to claim 6 or a vector comprising the polynucleotide; and
 (iii) administering the T cells or NK cells from (ii) to a subject.

12. A method according to claim 10, which involves monitoring toxic activity in the subject and comprises the step of administering the agent to the subject to reduce adverse toxic effects.

13. A method according to claim 11, which involves monitoring the progression of disease and/or monitoring toxic activity in the subject and comprises the step of administering the agent to the subject to provide acceptable levels of disease progression and/or toxic activity.

14. A method according to claim 10, wherein the subject has is cancer.

15. A method for making a T cell or NK cell, which comprises the step of introducing a polynucleotide according to claim 6 or a vector comprising the polynucleotide into a T or NK cell, wherein the T cell or NK cell expresses a CAR system,
wherein the CAR signalling system comprises:
 (i) a receptor component comprising an extracellular antigen binding domain, a spacer, a transmembrane domain, and a first intracellular binding domain; and
 (ii) an intracellular signalling component comprising a signalling domain and a second binding domain which specifically binds the first binding domain of the receptor component;
wherein the receptor component and signaling component are co-expressed;
wherein (i) and (ii) are separate molecules;
wherein binding of the first and second binding domains of the CAR system is disruptable by the presence of an agent,
wherein, in the absence of the agent, the receptor component and the intracellular signalling component heterodimerize, and binding of the antigen binding domain to antigen results in signalling through the signalling domain, whereas in the presence of the agent, the receptor component and the signalling component do not heterodimerize, and binding of the antigen binding domain to antigen does not result in signalling through the signalling domain; and
wherein the first intracellular binding domain comprises Tet Repressor Protein (TetR) or a variant thereof and the second binding domain comprises Transcription inducing peptide (TiP) or a variant thereof; or wherein the first intracellular binding domain comprises TiP or a variant thereof and the second binding domain comprises TetR or a variant thereof; and the agent is tetracycline, doxycycline or minocycline or an analogue thereof.

16. A method for inhibiting the CAR signalling system according to claim 1 in a subject to whom a T or NK cell that expresses said CAR system has been administered, which method comprises the step of administering the agent to the subject.

\* \* \* \* \*

UNITED STATES PATENT AND TRADEMARK OFFICE
CERTIFICATE OF CORRECTION

Page 1 of 1

PATENT NO. : 10,654,927 B2
APPLICATION NO. : 15/506383
DATED : May 19, 2020
INVENTOR(S) : Martin Pulé et al.

It is certified that error appears in the above-identified patent and that said Letters Patent is hereby corrected as shown below:

In the Claims

At Column 49, Line 57, "comprising;" should be -- comprising: --.

At Column 50, Line 56, "first and second binding" should be -- first intracellular and second binding --.

At Column 50, Line 58, "agent," should be -- agent; --.

At Column 51, Lines 19-20, "first binding" should be -- first intracellular binding --.

At Column 51, Lines 23-24, "first binding" should be -- first intracellular binding --.

At Column 51, Line 39, "first and second binding" should be -- first intracellular and second binding --.

At Column 51, Line 41, "agent," should be -- agent; --.

At Column 51, Line 48, "agent," should be -- agent; --.

At Column 52, Line 27, "has is" should be -- has --.

At Column 52, Line 41, "first binding" should be -- first intracellular binding --.

At Column 52, Line 46, "first and second binding" should be -- first intracellular and second binding --.

Signed and Sealed this
Second Day of March, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 29

<210> SEQ ID NO 1
<211> LENGTH: 139
<212> TYPE: PRT
<213> ORGANISM: Artificial Sequence
<220> FEATURE:
<223> OTHER INFORMATION: TetR binding domain

<400> SEQUENCE: 1

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65              70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His
    130                 135

<210> SEQ ID NO 2
<211> LENGTH: 17
<212> TYPE: PRT
<213> ORGANISM: Artificial Sequence
<220> FEATURE:
<223> OTHER INFORMATION: TiP binding domain

<400> SEQUENCE: 2

Met Trp Thr Trp Asn Ala Tyr Ala Phe Ala Ala Pro Ser Gly Gly Gly
1               5                   10                  15

Ser

<210> SEQ ID NO 3
<211> LENGTH: 61
<212> TYPE: PRT
<213> ORGANISM: Artificial Sequence
<220> FEATURE:
<223> OTHER INFORMATION: Modified CD4 endodomain linker

<400> SEQUENCE: 3

Ala Leu Ile Val Leu Gly Gly Val Ala Gly Leu Leu Leu Phe Ile Gly
1               5                   10                  15

Leu Gly Ile Phe Phe Cys Val Arg Cys Arg His Arg Arg Arg Gln Ala
            20                  25                  30

Glu Arg Met Ala Gln Ile Lys Arg Val Val Ser Glu Lys Lys Thr Ala
        35                  40                  45

Gln Ala Pro His Arg Phe Gln Lys Thr Cys Ser Pro Ile
    50                  55                  60

```
<210> SEQ ID NO 4
<211> LENGTH: 15
<212> TYPE: PRT
<213> ORGANISM: Artificial Sequence
<220> FEATURE:
<223> OTHER INFORMATION: Biotin mimicking peptide, long nanotag

<400> SEQUENCE: 4

Asp Val Glu Ala Trp Leu Asp Glu Arg Val Pro Leu Val Glu Thr
1               5                   10                  15

<210> SEQ ID NO 5
<211> LENGTH: 9
<212> TYPE: PRT
<213> ORGANISM: Artificial Sequence
<220> FEATURE:
<223> OTHER INFORMATION: Biotin mimicking peptide, short nanotag

<400> SEQUENCE: 5

Asp Val Glu Ala Trp Leu Gly Ala Arg
1               5

<210> SEQ ID NO 6
<211> LENGTH: 8
<212> TYPE: PRT
<213> ORGANISM: Artificial Sequence
<220> FEATURE:
<223> OTHER INFORMATION: Biotin mimicking peptide, streptag

<400> SEQUENCE: 6

Trp Arg His Pro Gln Phe Gly Gly
1               5

<210> SEQ ID NO 7
<211> LENGTH: 8
<212> TYPE: PRT
<213> ORGANISM: Artificial Sequence
<220> FEATURE:
<223> OTHER INFORMATION: Biotin mimicking peptide, streptagII

<400> SEQUENCE: 7

Trp Ser His Pro Gln Phe Glu Lys
1               5

<210> SEQ ID NO 8
<211> LENGTH: 38
<212> TYPE: PRT
<213> ORGANISM: Artificial Sequence
<220> FEATURE:
<223> OTHER INFORMATION: Biotin mimicking peptide, SBP-tag

<400> SEQUENCE: 8

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 9
<211> LENGTH: 8
<212> TYPE: PRT
<213> ORGANISM: Artificial Sequence
<220> FEATURE:
<223> OTHER INFORMATION: Biotin mimicking peptide, ccstreptag
```

<400> SEQUENCE: 9

Cys His Pro Gln Gly Pro Pro Cys
1               5

<210> SEQ ID NO 10
<211> LENGTH: 15
<212> TYPE: PRT
<213> ORGANISM: Artificial Sequence
<220> FEATURE:
<223> OTHER INFORMATION: Biotin mimicking peptide, flankedccstreptag

<400> SEQUENCE: 10

Ala Glu Cys His Pro Gln Gly Pro Pro Cys Ile Glu Gly Arg Lys
1               5                   10                  15

<210> SEQ ID NO 11
<211> LENGTH: 126
<212> TYPE: PRT
<213> ORGANISM: Artificial Sequence
<220> FEATURE:
<223> OTHER INFORMATION: Core streptavidin sequence

<400> SEQUENCE: 11

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Glu Ser
            20                  25                  30

Ala Val Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
        115                 120                 125

<210> SEQ ID NO 12
<211> LENGTH: 21
<212> TYPE: PRT
<213> ORGANISM: Artificial Sequence
<220> FEATURE:
<223> OTHER INFORMATION: signal peptide

<400> SEQUENCE: 12

Met Gly Thr Ser Leu Leu Cys Trp Met Ala Leu Cys Leu Leu Gly Ala
1               5                   10                  15

Asp His Ala Asp Gly
            20

<210> SEQ ID NO 13
<211> LENGTH: 21
<212> TYPE: PRT
<213> ORGANISM: Artificial Sequence
<220> FEATURE:
<223> OTHER INFORMATION: signal peptide

<400> SEQUENCE: 13

Met Ser Leu Pro Val Thr Ala Leu Leu Leu Pro Leu Ala Leu Leu Leu

His Ala Ala Arg Pro
            20

<210> SEQ ID NO 14
<211> LENGTH: 20
<212> TYPE: PRT
<213> ORGANISM: Artificial Sequence
<220> FEATURE:
<223> OTHER INFORMATION: signal peptide

<400> SEQUENCE: 14

Met Ala Val Pro Thr Gln Val Leu Gly Leu Leu Leu Leu Trp Leu Thr
1               5                   10                  15

Asp Ala Arg Cys
            20

<210> SEQ ID NO 15
<211> LENGTH: 234
<212> TYPE: PRT
<213> ORGANISM: Artificial Sequence
<220> FEATURE:
<223> OTHER INFORMATION: spacer sequence, hinge-CH2CH3 of human IgG1

<400> SEQUENCE: 15

Ala Glu Pro Lys Ser Pro Asp Lys Thr His Thr Cys Pro Pro Cys Pro
1               5                   10                  15

Ala Pro Pro Val Ala Gly Pro Ser Val Phe Leu Phe Pro Pro Lys Pro
                20                  25                  30

Lys Asp Thr Leu Met Ile Ala Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys Lys Asp
225                 230

<210> SEQ ID NO 16
<211> LENGTH: 46

```
<212> TYPE: PRT
<213> ORGANISM: Artificial Sequence
<220> FEATURE:
<223> OTHER INFORMATION: spacer sequence, human CD8 stalk

<400> SEQUENCE: 16

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile
        35                  40                  45

<210> SEQ ID NO 17
<211> LENGTH: 20
<212> TYPE: PRT
<213> ORGANISM: Artificial Sequence
<220> FEATURE:
<223> OTHER INFORMATION: spacer sequence, human IgG1 hinge

<400> SEQUENCE: 17

Ala Glu Pro Lys Ser Pro Asp Lys Thr His Thr Cys Pro Pro Cys Pro
1               5                   10                  15

Lys Asp Pro Lys
            20

<210> SEQ ID NO 18
<211> LENGTH: 185
<212> TYPE: PRT
<213> ORGANISM: Artificial Sequence
<220> FEATURE:
<223> OTHER INFORMATION: spacer sequence, CD2 ectodomain

<400> SEQUENCE: 18

Lys Glu Ile Thr Asn Ala Leu Glu Thr Trp Gly Ala Leu Gly Gln Asp
1               5                   10                  15

Ile Asn Leu Asp Ile Pro Ser Phe Gln Met Ser Asp Asp Ile Asp Asp
            20                  25                  30

Ile Lys Trp Glu Lys Thr Ser Asp Lys Lys Lys Ile Ala Gln Phe Arg
        35                  40                  45

Lys Glu Lys Glu Thr Phe Lys Glu Lys Asp Thr Tyr Lys Leu Phe Lys
    50                  55                  60

Asn Gly Thr Leu Lys Ile Lys His Leu Lys Thr Asp Asp Gln Asp Ile
65                  70                  75                  80

Tyr Lys Val Ser Ile Tyr Asp Thr Lys Gly Lys Asn Val Leu Glu Lys
                85                  90                  95

Ile Phe Asp Leu Lys Ile Gln Glu Arg Val Ser Lys Pro Lys Ile Ser
            100                 105                 110

Trp Thr Cys Ile Asn Thr Thr Leu Thr Cys Glu Val Met Asn Gly Thr
        115                 120                 125

Asp Pro Glu Leu Asn Leu Tyr Gln Asp Gly Lys His Leu Lys Leu Ser
    130                 135                 140

Gln Arg Val Ile Thr His Lys Trp Thr Thr Ser Leu Ser Ala Lys Phe
145                 150                 155                 160

Lys Cys Thr Ala Gly Asn Lys Val Ser Lys Glu Ser Ser Val Glu Pro
                165                 170                 175

Val Ser Cys Pro Glu Lys Gly Leu Asp
            180                 185
```

```
<210> SEQ ID NO 19
<211> LENGTH: 259
<212> TYPE: PRT
<213> ORGANISM: Artificial Sequence
<220> FEATURE:
<223> OTHER INFORMATION: spacer sequence, CD34 ectodomain

<400> SEQUENCE: 19

Ser Leu Asp Asn Asn Gly Thr Ala Thr Pro Glu Leu Pro Thr Gln Gly
1               5                   10                  15

Thr Phe Ser Asn Val Ser Thr Asn Val Ser Tyr Gln Glu Thr Thr Thr
            20                  25                  30

Pro Ser Thr Leu Gly Ser Thr Ser Leu His Pro Val Ser Gln His Gly
        35                  40                  45

Asn Glu Ala Thr Thr Asn Ile Thr Glu Thr Thr Val Lys Phe Thr Ser
    50                  55                  60

Thr Ser Val Ile Thr Ser Val Tyr Gly Asn Thr Asn Ser Ser Val Gln
65                  70                  75                  80

Ser Gln Thr Ser Val Ile Ser Thr Val Phe Thr Thr Pro Ala Asn Val
                85                  90                  95

Ser Thr Pro Glu Thr Thr Leu Lys Pro Ser Leu Ser Pro Gly Asn Val
            100                 105                 110

Ser Asp Leu Ser Thr Thr Ser Thr Ser Leu Ala Thr Ser Pro Thr Lys
        115                 120                 125

Pro Tyr Thr Ser Ser Ser Pro Ile Leu Ser Asp Ile Lys Ala Glu Ile
    130                 135                 140

Lys Cys Ser Gly Ile Arg Glu Val Lys Leu Thr Gln Gly Ile Cys Leu
145                 150                 155                 160

Glu Gln Asn Lys Thr Ser Ser Cys Ala Glu Phe Lys Lys Asp Arg Gly
                165                 170                 175

Glu Gly Leu Ala Arg Val Leu Cys Gly Glu Glu Gln Ala Asp Ala Asp
            180                 185                 190

Ala Gly Ala Gln Val Cys Ser Leu Leu Leu Ala Gln Ser Glu Val Arg
        195                 200                 205

Pro Gln Cys Leu Leu Leu Val Leu Ala Asn Arg Thr Glu Ile Ser Ser
    210                 215                 220

Lys Leu Gln Leu Met Lys Lys His Gln Ser Asp Leu Lys Lys Leu Gly
225                 230                 235                 240

Ile Leu Asp Phe Thr Glu Gln Asp Val Ala Ser His Gln Ser Tyr Ser
                245                 250                 255

Gln Lys Thr

<210> SEQ ID NO 20
<211> LENGTH: 112
<212> TYPE: PRT
<213> ORGANISM: Artificial Sequence
<220> FEATURE:
<223> OTHER INFORMATION: signalling component, CD3 Z endodomain

<400> SEQUENCE: 20

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
```

```
                50                  55                  60
Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
            100                 105                 110
```

<210> SEQ ID NO 21
<211> LENGTH: 152
<212> TYPE: PRT
<213> ORGANISM: Artificial Sequence
<220> FEATURE:
<223> OTHER INFORMATION: signalling component, CD28 and CD3 Zeta
      endodomains

<400> SEQUENCE: 21

```
Ser Lys Arg Ser Arg Leu Leu His Ser Asp Tyr Met Asn Met Thr Pro
 1               5                  10                  15

Arg Arg Pro Gly Pro Thr Arg Lys His Tyr Gln Pro Tyr Ala Pro Pro
                20                  25                  30

Arg Asp Phe Ala Ala Tyr Arg Ser Arg Val Lys Phe Ser Arg Ser Ala
             35                  40                  45

Asp Ala Pro Ala Tyr Gln Gln Gly Gln Asn Gln Leu Tyr Asn Glu Leu
 50                  55                  60

Asn Leu Gly Arg Arg Glu Glu Tyr Asp Val Leu Asp Lys Arg Arg Gly
 65                  70                  75                  80

Arg Asp Pro Glu Met Gly Gly Lys Pro Arg Arg Lys Asn Pro Gln Glu
                 85                  90                  95

Gly Leu Tyr Asn Glu Leu Gln Lys Asp Lys Met Ala Glu Ala Tyr Ser
            100                 105                 110

Glu Ile Gly Met Lys Gly Glu Arg Arg Arg Gly Lys Gly His Asp Gly
            115                 120                 125

Leu Tyr Gln Gly Leu Ser Thr Ala Thr Lys Asp Thr Tyr Asp Ala Leu
            130                 135                 140

His Met Gln Ala Leu Pro Pro Arg
145                 150
```

<210> SEQ ID NO 22
<211> LENGTH: 188
<212> TYPE: PRT
<213> ORGANISM: Artificial Sequence
<220> FEATURE:
<223> OTHER INFORMATION: signalling component, CD28, OX40 and CD3 Zeta
      endodomains

<400> SEQUENCE: 22

```
Ser Lys Arg Ser Arg Leu Leu His Ser Asp Tyr Met Asn Met Thr Pro
 1               5                  10                  15

Arg Arg Pro Gly Pro Thr Arg Lys His Tyr Gln Pro Tyr Ala Pro Pro
                20                  25                  30

Arg Asp Phe Ala Ala Tyr Arg Ser Arg Asp Gln Arg Leu Pro Pro Asp
             35                  40                  45

Ala His Lys Pro Pro Gly Gly Gly Ser Phe Arg Thr Pro Ile Gln Glu
 50                  55                  60

Glu Gln Ala Asp Ala His Ser Thr Leu Ala Lys Ile Arg Val Lys Phe
 65                  70                  75                  80

Ser Arg Ser Ala Asp Ala Pro Ala Tyr Gln Gln Gly Gln Asn Gln Leu
```

```
                        85                  90                  95

Tyr Asn Glu Leu Asn Leu Gly Arg Arg Glu Glu Tyr Asp Val Leu Asp
                100                 105                 110

Lys Arg Arg Gly Arg Asp Pro Glu Met Gly Gly Lys Pro Arg Arg Lys
            115                 120                 125

Asn Pro Gln Glu Gly Leu Tyr Asn Glu Leu Gln Lys Asp Lys Met Ala
        130                 135                 140

Glu Ala Tyr Ser Glu Ile Gly Met Lys Gly Glu Arg Arg Arg Gly Lys
145                 150                 155                 160

Gly His Asp Gly Leu Tyr Gln Gly Leu Ser Thr Ala Thr Lys Asp Thr
                165                 170                 175

Tyr Asp Ala Leu His Met Gln Ala Leu Pro Pro Arg
            180                 185

<210> SEQ ID NO 23
<211> LENGTH: 20
<212> TYPE: PRT
<213> ORGANISM: Artificial Sequence
<220> FEATURE:
<223> OTHER INFORMATION: self-cleaving site, 2a self-cleaving peptide

<400> SEQUENCE: 23

Arg Ala Glu Gly Arg Gly Ser Leu Leu Thr Cys Gly Asp Val Glu Glu
1               5                   10                  15

Asn Pro Gly Pro
            20

<210> SEQ ID NO 24
<211> LENGTH: 20
<212> TYPE: PRT
<213> ORGANISM: Artificial Sequence
<220> FEATURE:
<223> OTHER INFORMATION: self-cleaving site, 2a self-cleaving peptide

<400> SEQUENCE: 24

Gln Cys Thr Asn Tyr Ala Leu Leu Lys Leu Ala Gly Asp Val Glu Ser
1               5                   10                  15

Asn Pro Gly Pro
            20

<210> SEQ ID NO 25
<211> LENGTH: 652
<212> TYPE: PRT
<213> ORGANISM: Artificial Sequence
<220> FEATURE:
<223> OTHER INFORMATION: chimeric antigen receptor (CAR) sequence

<400> SEQUENCE: 25

Met Trp Thr Trp Asn Ala Tyr Ala Phe Ala Ala Pro Ser Gly Gly Gly
1               5                   10                  15

Ser Ala Asp Ala Pro Ala Tyr Gln Gln Gly Gln Asn Gln Leu Tyr Asn
            20                  25                  30

Glu Leu Asn Leu Gly Arg Arg Glu Glu Tyr Asp Val Leu Asp Lys Arg
        35                  40                  45

Arg Gly Arg Asp Pro Glu Met Gly Gly Lys Pro Arg Arg Lys Asn Pro
    50                  55                  60

Gln Glu Gly Leu Tyr Asn Glu Leu Gln Lys Asp Lys Met Ala Glu Ala
65                  70                  75                  80

Tyr Ser Glu Ile Gly Met Lys Gly Glu Arg Arg Arg Gly Lys Gly His
                85                  90                  95
```

```
Asp Gly Leu Tyr Gln Gly Leu Ser Thr Ala Thr Lys Asp Thr Tyr Asp
            100                 105                 110

Ala Leu His Met Gln Ala Leu Pro Arg Arg Ala Glu Gly Arg Gly
        115                 120                 125

Ser Leu Leu Thr Cys Gly Asp Val Glu Glu Asn Pro Gly Pro Met Ala
    130                 135                 140

Val Pro Thr Gln Val Leu Gly Leu Leu Leu Trp Leu Thr Asp Ala
145                 150                 155                 160

Arg Cys Asp Ile Gln Met Thr Gln Ser Pro Ser Ser Leu Ser Ala Ser
                165                 170                 175

Val Gly Asp Arg Val Thr Ile Thr Cys Arg Ala Ser Glu Asp Ile Tyr
            180                 185                 190

Phe Asn Leu Val Trp Tyr Gln Gln Lys Pro Gly Lys Ala Pro Lys Leu
        195                 200                 205

Leu Ile Tyr Asp Thr Asn Arg Leu Ala Asp Gly Val Pro Ser Arg Phe
    210                 215                 220

Ser Gly Ser Gly Ser Gly Thr Gln Tyr Thr Leu Thr Ile Ser Ser Leu
225                 230                 235                 240

Gln Pro Glu Asp Phe Ala Thr Tyr Tyr Cys Gln His Tyr Lys Asn Tyr
                245                 250                 255

Pro Leu Thr Phe Gly Gln Gly Thr Lys Leu Glu Ile Lys Arg Ser Gly
            260                 265                 270

Gly Gly Gly Ser Gly Gly Gly Ser Gly Gly Gly Ser Gly Gly
        275                 280                 285

Gly Gly Ser Arg Ser Glu Val Gln Leu Val Glu Ser Gly Gly Gly Leu
            290                 295                 300

Val Gln Pro Gly Gly Ser Leu Arg Leu Ser Cys Ala Ala Ser Gly Phe
305                 310                 315                 320

Thr Leu Ser Asn Tyr Gly Met His Trp Ile Arg Gln Ala Pro Gly Lys
                325                 330                 335

Gly Leu Glu Trp Val Ser Ser Ile Ser Leu Asn Gly Gly Ser Thr Tyr
            340                 345                 350

Tyr Arg Asp Ser Val Lys Gly Arg Phe Thr Ile Ser Arg Asp Asn Ala
        355                 360                 365

Lys Ser Thr Leu Tyr Leu Gln Met Asn Ser Leu Arg Ala Glu Asp Thr
    370                 375                 380

Ala Val Tyr Tyr Cys Ala Ala Gln Asp Ala Tyr Thr Gly Gly Tyr Phe
385                 390                 395                 400

Asp Tyr Trp Gly Gln Gly Thr Leu Val Thr Val Ser Ser Met Asp Pro
                405                 410                 415

Ala Glu Pro Lys Ser Pro Asp Lys Thr His Thr Cys Pro Pro Cys Pro
            420                 425                 430

Ala Pro Pro Val Ala Gly Pro Ser Val Phe Leu Phe Pro Pro Lys Pro
        435                 440                 445

Lys Asp Thr Leu Met Ile Ala Arg Thr Pro Glu Val Thr Cys Val Val
    450                 455                 460

Val Asp Val Ser His Glu Asp Pro Glu Val Lys Phe Asn Trp Tyr Val
465                 470                 475                 480

Asp Gly Val Glu Val His Asn Ala Lys Thr Lys Pro Arg Glu Glu Gln
                485                 490                 495

Tyr Asn Ser Thr Tyr Arg Val Val Ser Val Leu Thr Val Leu His Gln
            500                 505                 510
```

Asp Trp Leu Asn Gly Lys Glu Tyr Lys Cys Lys Val Ser Asn Lys Ala
            515                 520                 525

Leu Pro Ala Pro Ile Glu Lys Thr Ile Ser Lys Ala Lys Gly Gln Pro
        530                 535                 540

Arg Glu Pro Gln Val Tyr Thr Leu Pro Pro Ser Arg Asp Glu Leu Thr
545                 550                 555                 560

Lys Asn Gln Val Ser Leu Thr Cys Leu Val Lys Gly Phe Tyr Pro Ser
                565                 570                 575

Asp Ile Ala Val Glu Trp Glu Ser Asn Gly Gln Pro Glu Asn Asn Tyr
            580                 585                 590

Lys Thr Thr Pro Pro Val Leu Asp Ser Asp Gly Ser Phe Phe Leu Tyr
        595                 600                 605

Ser Lys Leu Thr Val Asp Lys Ser Arg Trp Gln Gln Gly Asn Val Phe
        610                 615                 620

Ser Cys Ser Val Met His Glu Ala Leu His Asn His Tyr Thr Gln Lys
625                 630                 635                 640

Ser Leu Ser Leu Ser Pro Gly Lys Lys Asp Pro Met
                645                 650

<210> SEQ ID NO 26
<211> LENGTH: 213
<212> TYPE: PRT
<213> ORGANISM: Artificial Sequence
<220> FEATURE:
<223> OTHER INFORMATION: chimeric antigen receptor (CAR) sequence

<400> SEQUENCE: 26

Ser Gly Gly Gly Gly Ser Met Ser Arg Leu Asp Lys Ser Lys Val Ile
1               5                   10                  15

Asn Ser Ala Leu Glu Leu Leu Asn Glu Val Gly Ile Glu Gly Leu Thr
            20                  25                  30

Thr Arg Lys Leu Ala Gln Lys Leu Gly Val Glu Gln Pro Thr Leu Tyr
        35                  40                  45

Trp His Val Lys Asn Lys Arg Ala Leu Leu Asp Ala Leu Ala Ile Glu
    50                  55                  60

Met Leu Asp Arg His His Thr His Phe Cys Pro Leu Glu Gly Glu Ser
65                  70                  75                  80

Trp Gln Asp Phe Leu Arg Asn Asn Ala Lys Ser Phe Arg Cys Ala Leu
                85                  90                  95

Leu Ser His Arg Asp Gly Ala Lys Val His Leu Gly Thr Arg Pro Thr
            100                 105                 110

Glu Lys Gln Tyr Glu Thr Leu Glu Asn Gln Leu Ala Phe Leu Cys Gln
        115                 120                 125

Gln Gly Phe Ser Leu Glu Asn Ala Leu Tyr Ala Leu Ser Ala Val Gly
    130                 135                 140

His Phe Thr Leu Gly Cys Val Leu Glu Asp Gln Glu His Gln Val Ala
145                 150                 155                 160

Lys Glu Glu Arg Glu Thr Pro Thr Thr Asp Ser Met Pro Pro Leu Leu
                165                 170                 175

Arg Gln Ala Ile Glu Leu Phe Asp His Gln Gly Ala Glu Pro Ala Phe
            180                 185                 190

Leu Phe Gly Leu Glu Leu Ile Ile Cys Gly Leu Glu Lys Gln Leu Lys
        195                 200                 205

Cys Glu Ser Gly Ser
    210

<210> SEQ ID NO 27
<211> LENGTH: 16
<212> TYPE: PRT
<213> ORGANISM: Artificial Sequence
<220> FEATURE:
<223> OTHER INFORMATION: sequence of TiP

<400> SEQUENCE: 27

Trp Thr Trp Asn Ala Tyr Ala Phe Ala Ala Pro Ser Gly Gly Gly Ser
1               5                   10                  15

<210> SEQ ID NO 28
<211> LENGTH: 87
<212> TYPE: PRT
<213> ORGANISM: Homo sapiens

<400> SEQUENCE: 28

Leu Ser Asp Ser Gly Gln Val Leu Leu Glu Ser Asn Ile Lys Val Leu
1               5                   10                  15

Pro Thr Trp Ser Thr Pro Val Gln Pro Met Ala Leu Ile Val Leu Gly
                20                  25                  30

Gly Val Ala Gly Leu Leu Leu Phe Ile Gly Leu Gly Ile Phe Phe Cys
            35                  40                  45

Val Arg Cys Arg His Arg Arg Arg Gln Ala Glu Arg Met Ser Gln Ile
    50                  55                  60

Lys Arg Leu Leu Ser Glu Lys Lys Thr Cys Gln Cys Pro His Arg Phe
65                  70                  75                  80

Gln Lys Thr Cys Ser Pro Ile
                85

<210> SEQ ID NO 29
<211> LENGTH: 926
<212> TYPE: PRT
<213> ORGANISM: Artificial Sequence
<220> FEATURE:
<223> OTHER INFORMATION: basic TetCAR sequence

<400> SEQUENCE: 29

Met Trp Thr Trp Asn Ala Tyr Ala Phe Ala Ala Pro Ser Gly Gly Gly
1               5                   10                  15

Ser Ala Asp Ala Pro Ala Tyr Gln Gln Gly Gln Asn Gln Leu Tyr Asn
                20                  25                  30

Glu Leu Asn Leu Gly Arg Arg Glu Glu Tyr Asp Val Leu Asp Lys Arg
            35                  40                  45

Arg Gly Arg Asp Pro Glu Met Gly Gly Lys Pro Arg Arg Lys Asn Pro
    50                  55                  60

Gln Glu Gly Leu Tyr Asn Glu Leu Gln Lys Asp Lys Met Ala Glu Ala
65                  70                  75                  80

Tyr Ser Glu Ile Gly Met Lys Gly Glu Arg Arg Arg Gly Lys Gly His
                85                  90                  95

Asp Gly Leu Tyr Gln Gly Leu Ser Thr Ala Thr Lys Asp Thr Tyr Asp
                100                 105                 110

Ala Leu His Met Gln Ala Leu Pro Pro Arg Arg Ala Glu Gly Arg Gly
            115                 120                 125

Ser Leu Leu Thr Cys Gly Asp Val Glu Glu Asn Pro Gly Pro Met Ala
    130                 135                 140

Val Pro Thr Gln Val Leu Gly Leu Leu Leu Leu Trp Leu Thr Asp Ala
145                 150                 155                 160

```
Arg Cys Asp Ile Gln Met Thr Gln Ser Pro Ser Ser Leu Ser Ala Ser
                165                 170                 175
Val Gly Asp Arg Val Thr Ile Thr Cys Arg Ala Ser Glu Asp Ile Tyr
            180                 185                 190
Phe Asn Leu Val Trp Tyr Gln Gln Lys Pro Gly Lys Ala Pro Lys Leu
        195                 200                 205
Leu Ile Tyr Asp Thr Asn Arg Leu Ala Asp Gly Val Pro Ser Arg Phe
    210                 215                 220
Ser Gly Ser Gly Ser Gly Thr Gln Tyr Thr Leu Thr Ile Ser Ser Leu
225                 230                 235                 240
Gln Pro Glu Asp Phe Ala Thr Tyr Tyr Cys Gln His Tyr Lys Asn Tyr
                245                 250                 255
Pro Leu Thr Phe Gly Gln Gly Thr Lys Leu Glu Ile Lys Arg Ser Gly
            260                 265                 270
Gly Gly Gly Ser Gly Gly Gly Ser Gly Gly Gly Ser Gly Gly Gly Gly
        275                 280                 285
Gly Gly Ser Arg Ser Glu Val Gln Leu Val Glu Ser Gly Gly Gly Leu
    290                 295                 300
Val Gln Pro Gly Gly Ser Leu Arg Leu Ser Cys Ala Ala Ser Gly Phe
305                 310                 315                 320
Thr Leu Ser Asn Tyr Gly Met His Trp Ile Arg Gln Ala Pro Gly Lys
                325                 330                 335
Gly Leu Glu Trp Val Ser Ser Ile Ser Leu Asn Gly Gly Ser Thr Tyr
            340                 345                 350
Tyr Arg Asp Ser Val Lys Gly Arg Phe Thr Ile Ser Arg Asp Asn Ala
        355                 360                 365
Lys Ser Thr Leu Tyr Leu Gln Met Asn Ser Leu Arg Ala Glu Asp Thr
    370                 375                 380
Ala Val Tyr Tyr Cys Ala Ala Gln Asp Ala Tyr Thr Gly Gly Tyr Phe
385                 390                 395                 400
Asp Tyr Trp Gly Gln Gly Thr Leu Val Thr Val Ser Ser Met Asp Pro
                405                 410                 415
Ala Glu Pro Lys Ser Pro Asp Lys Thr His Thr Cys Pro Pro Cys Pro
            420                 425                 430
Ala Pro Pro Val Ala Gly Pro Ser Val Phe Leu Phe Pro Pro Lys Pro
        435                 440                 445
Lys Asp Thr Leu Met Ile Ala Arg Thr Pro Glu Val Thr Cys Val Val
    450                 455                 460
Val Asp Val Ser His Glu Asp Pro Glu Val Lys Phe Asn Trp Tyr Val
465                 470                 475                 480
Asp Gly Val Glu Val His Asn Ala Lys Thr Lys Pro Arg Glu Glu Gln
                485                 490                 495
Tyr Asn Ser Thr Tyr Arg Val Val Ser Val Leu Thr Val Leu His Gln
            500                 505                 510
Asp Trp Leu Asn Gly Lys Glu Tyr Lys Cys Lys Val Ser Asn Lys Ala
        515                 520                 525
Leu Pro Ala Pro Ile Glu Lys Thr Ile Ser Lys Ala Lys Gly Gln Pro
    530                 535                 540
Arg Glu Pro Gln Val Tyr Thr Leu Pro Pro Ser Arg Asp Glu Leu Thr
545                 550                 555                 560
Lys Asn Gln Val Ser Leu Thr Cys Leu Val Lys Gly Phe Tyr Pro Ser
                565                 570                 575
Asp Ile Ala Val Glu Trp Glu Ser Asn Gly Gln Pro Glu Asn Asn Tyr
```

-continued

```
                580                 585                 590
Lys Thr Thr Pro Pro Val Leu Asp Ser Asp Gly Ser Phe Phe Leu Tyr
        595                 600                 605

Ser Lys Leu Thr Val Asp Lys Ser Arg Trp Gln Gln Gly Asn Val Phe
        610                 615                 620

Ser Cys Ser Val Met His Glu Ala Leu His Asn His Tyr Thr Gln Lys
625                 630                 635                 640

Ser Leu Ser Leu Ser Pro Gly Lys Lys Asp Pro Met Ala Leu Ile Val
                645                 650                 655

Leu Gly Gly Val Ala Gly Leu Leu Leu Phe Ile Gly Leu Gly Ile Phe
                660                 665                 670

Phe Cys Val Arg Cys Arg His Arg Arg Arg Gln Ala Glu Arg Met Ala
        675                 680                 685

Gln Ile Lys Arg Val Val Ser Glu Lys Lys Thr Ala Gln Ala Pro His
        690                 695                 700

Arg Phe Gln Lys Thr Cys Ser Pro Ile Ser Gly Gly Gly Ser Met
705                 710                 715                 720

Ser Arg Leu Asp Lys Ser Lys Val Ile Asn Ser Ala Leu Glu Leu Leu
                725                 730                 735

Asn Glu Val Gly Ile Glu Gly Leu Thr Thr Arg Lys Leu Ala Gln Lys
                740                 745                 750

Leu Gly Val Glu Gln Pro Thr Leu Tyr Trp His Val Lys Asn Lys Arg
                755                 760                 765

Ala Leu Leu Asp Ala Leu Ala Ile Glu Met Leu Asp Arg His His Thr
        770                 775                 780

His Phe Cys Pro Leu Glu Gly Glu Ser Trp Gln Asp Phe Leu Arg Asn
785                 790                 795                 800

Asn Ala Lys Ser Phe Arg Cys Ala Leu Leu Ser His Arg Asp Gly Ala
                805                 810                 815

Lys Val His Leu Gly Thr Arg Pro Thr Glu Lys Gln Tyr Glu Thr Leu
                820                 825                 830

Glu Asn Gln Leu Ala Phe Leu Cys Gln Gln Gly Phe Ser Leu Glu Asn
        835                 840                 845

Ala Leu Tyr Ala Leu Ser Ala Val Gly His Phe Thr Leu Gly Cys Val
        850                 855                 860

Leu Glu Asp Gln Glu His Gln Val Ala Lys Glu Glu Arg Glu Thr Pro
865                 870                 875                 880

Thr Thr Asp Ser Met Pro Pro Leu Leu Arg Gln Ala Ile Glu Leu Phe
                885                 890                 895

Asp His Gln Gly Ala Glu Pro Ala Phe Leu Phe Gly Leu Glu Leu Ile
                900                 905                 910

Ile Cys Gly Leu Glu Lys Gln Leu Lys Cys Glu Ser Gly Ser
                915                 920                 925
```